(12) United States Patent
Stegmann

(10) Patent No.: US 12,740,889 B2
(45) Date of Patent: Sep. 22, 2026

(54) APPARATUS FOR THERMAL THERAPY TREATMENT OF A SELECTED REGION OF THE BODY OF A HUMAN OR OF AN ANIMAL AND METHOD OF OPERATING SAID APPARATUS

(71) Applicant: HILOTHERM HOLDING AG, Oberwil b. Zug (CH)

(72) Inventor: Christian Stegmann, Burgberg im Allgäu (DE)

(73) Assignee: HILOTHERM HOLDING AG, Oberwil b. Zug (CH)

( * ) Notice: Subject to any disclaimer, the term of this patent is extended or adjusted under 35 U.S.C. 154(b) by 626 days.

(21) Appl. No.: 18/252,332

(22) PCT Filed: Nov. 11, 2021

(86) PCT No.: PCT/EP2021/081335
§ 371 (c)(1),
(2) Date: May 9, 2023

(87) PCT Pub. No.: WO2022/101320
PCT Pub. Date: May 19, 2022

(65) Prior Publication Data

US 2024/0009026 A1 Jan. 11, 2024

Related U.S. Application Data

(63) Continuation of application No. 17/365,957, filed on Jul. 1, 2021, now Pat. No. 12,409,061.

(30) Foreign Application Priority Data

Nov. 11, 2020 (EP) .................................... 20206941

(51) Int. Cl.
*A61F 7/02* (2006.01)
*A61F 7/00* (2006.01)

(52) U.S. Cl.
CPC .............. *A61F 7/02* (2013.01); *A61F 7/0085* (2013.01); *A61F 2007/0018* (2013.01);
(Continued)

(58) Field of Classification Search
CPC ...... A61F 2007/0018; A61F 2007/0036; A61F 2007/0045; A61F 2007/0054;
(Continued)

(56) References Cited

U.S. PATENT DOCUMENTS 4,951,665 A * 8/1990 Schneider ................. A61F 7/00 607/104
2011/0152982 A1* 6/2011 Richardson ............... A61F 7/02 607/104
(Continued)

FOREIGN PATENT DOCUMENTS

DE 102015003473 A1 9/2015
DE 102014012638 A1 2/2016
(Continued)

OTHER PUBLICATIONS

International Search Report and Written Opinion of the ISA for PCT/EP2021/081335 mailed Apr. 7, 2022, 22 pages.
(Continued)

*Primary Examiner* — Tigist S Demie
(74) *Attorney, Agent, or Firm* — Kilpatrick Townsend & Stockton LLP

(57) ABSTRACT

The invention relates to a device for use in the thermal therapy treatment of a selected region of the body of a human or of an animal, in particular for use in the treatment of tissue damage after surgical interventions, of injuries, of inflammations and of chronic diseases of the rheumatic type, and in particular for assisting chemotherapeutic treatments, comprising a temperature control device which is provided in order to control a temperature of a temperature control
(Continued)

fluid, and a heat transfer device which is arranged to transfer heat to the selected region of the body, wherein the temperature control device is connected, in a fluid conducting manner, to the heat transfer device, and is further arranged to temper the heat transfer device with a heat transferring temperature control fluid flowing through the heat transfer device, and with a control device which is connected to the temperature control device and to the heat transfer device, wherein the control device is arranged to control the temperature control device, in order to cause the heat transfer device to be at least partially at an approximately uniform temperature in the region of a contact surface between the heat transfer device and the selected region of the body to be temperature controlled. The invention further relates to a method of operating the device.

15 Claims, 6 Drawing Sheets

(52) U.S. Cl.
CPC ................ *A61F 2007/0055* (2013.01); *A61F 2007/0217* (2013.01); *A61F 2007/0252* (2013.01); *A61F 2007/0287* (2013.01)

(58) Field of Classification Search
CPC ...... A61F 2007/0055; A61F 2007/0217; A61F 2007/0252; A61F 2007/0287; A61F 7/0085; A61F 7/02; A61F 2007/0029; A61F 2007/0056; A61F 2007/0076; A61F 2007/0086; A61F 2007/0091; A61F 2007/0092; A61F 2007/0225; A61F 2007/0268; A61F 2007/0273; A61F 2007/0274; A61F 7/007
See application file for complete search history.

(56) References Cited

U.S. PATENT DOCUMENTS

2012/0172774 A1 7/2012 Lowe et al.
2013/0296981 A1 11/2013 Saggers
2015/0328042 A1 11/2015 Parish et al.
2016/0338873 A1 11/2016 Parish et al.
2017/0216129 A1* 8/2017 Lowe .................. A61H 9/0078
2019/0133817 A1 5/2019 Hilton et al.
2019/0240067 A1* 8/2019 Scott ......................... A61F 7/00
2020/0375793 A1 12/2020 Dilligan et al.

FOREIGN PATENT DOCUMENTS

DE 102017200034 A1 7/2018
DE 202018107423 U1 3/2020
EP 1972312 A2 9/2008
EP 2194940 B1 9/2011
EP 2462906 A1 6/2012
EP 2999441 3/2016
WO 2014188213 A2 11/2014
WO 2016016610 A1 2/2016

OTHER PUBLICATIONS

Extended European Search Report issued in EP Appln. No. 20206941.5 dated Apr. 19, 2021, 12 pages, including English translation.

"10-12° C., Hilotherapie, zur Vermeidung der Polyneuropathie (CIPN) and des Hand-Full-Syndroms (HFS)", Hilotherm GmbH, 5 pages (no translation provided).

U.S. Appl. No. 17/365,957, Final Office Action, Mailed Jan. 16, 2025, 20 pages.

Schaper T., "Polyneuropathie, Pilotprojekt belegt: Neuartige Hilotherapie, Vermeidet Schmerzhafte Nervenerkrankung", Available online at: https://hiloterapia.net/wp-content/uploads/Hilotherapie.pdf, 2018, 1 page (no translation provided).

Schaper T., "The Prophylactic Use of Hilotherapy® (Physical Thermotherapy) Prevents Chemotherapy Induced Peripheral Neuropathy (CIPN)", European Breast Cancer Institute, Available online at: https://www.hilotherm.com/wp-content/uploads/2020/07/2019-Chemo-Engl.pdf, Sep. 2019, 27 pages.

Schaper T., "Vermeidung der Chemotherapie-induzierten Polyneuropathie (CIPN)", Available online at: https://www.hilotherm.com/wp-content/uploads/2020/07/2020-Studie-Chemotherapie-Maerz-2020.pdf, 2020, 33 pages (no translation provided).

Schubert R., "Hilotherapy, The Thermal Procedure, Controllable to the Nearest Degree", Hilotherm GmbH, Wittumweg 38, 2016, 4 pages.

* cited by examiner

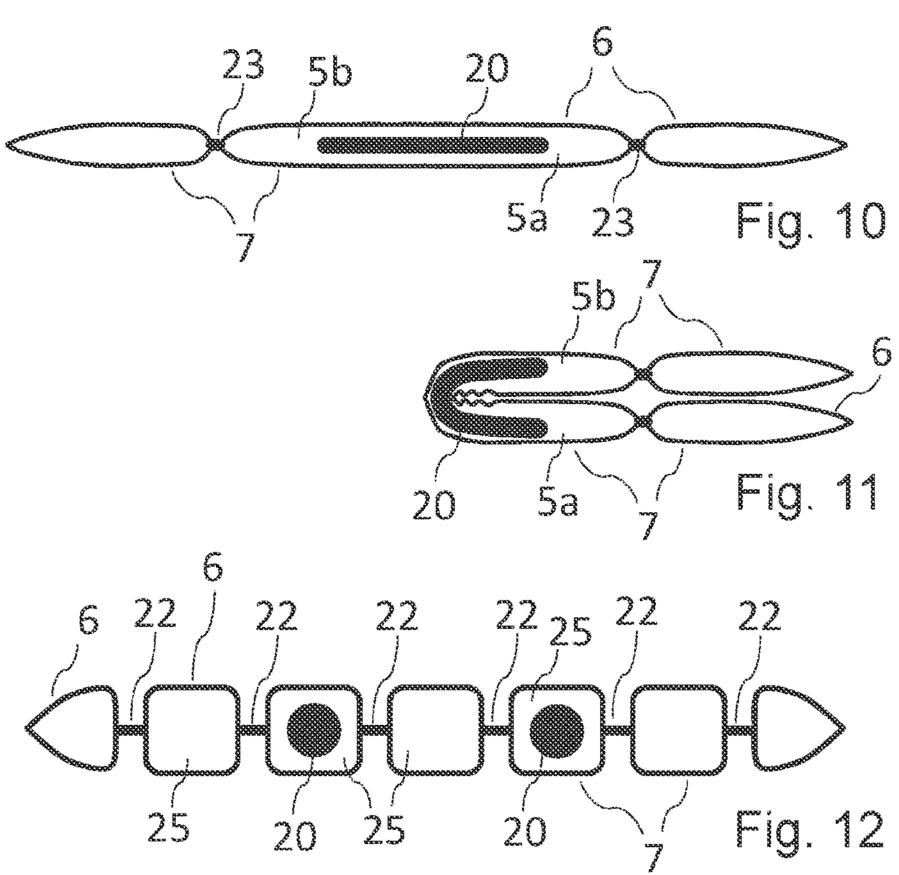
Fig. 10
Fig. 11
Fig. 12
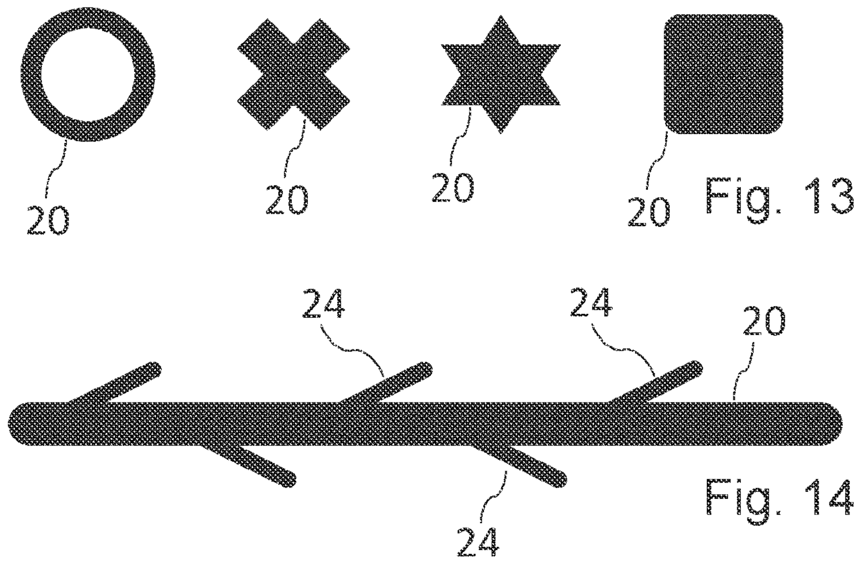
Fig. 13
Fig. 14

APPARATUS FOR THERMAL THERAPY TREATMENT OF A SELECTED REGION OF THE BODY OF A HUMAN OR OF AN ANIMAL AND METHOD OF OPERATING SAID APPARATUS

This application is the U.S. national phase of International Application No. PCT/EP2021/081335 filed Nov. 11, 2021, which designated the U.S. and claims priority to European Patent Application No. 20206941.5 filed Nov. 11, 2020 and U.S. patent application Ser. No. 17/365,957 filed Jul. 1, 2021, the entire contents of each of which are hereby incorporated by reference.

The present invention relates to a device for use in the thermal therapy treatment of a selected region of the body of a human or of an animal, and in particular for use in the treatment of tissue damage after surgical interventions, of injuries, of inflammations and of chronic diseases of the rheumatic type, and in particular for assisting chemotherapeutic treatments, as well as a method of operating such a device.

In the context of the present invention, the term “thermal therapy treatment” is intended to be understood to mean a treatment in which heat is supplied to the human or animal body, or removed therefrom.

Preferably, this is not a matter of supplying heat to, or removing heat from, the entire body, as is done, for example, in a sauna and the subsequent immersion in a plunge pool filled with cold water, but it is preferably a matter of supplying heat to, or removing heat from, a selected region of the human body, for example the limbs, regions of the back, the abdomen, the chest or the head, in order to achieve therapeutic effects.

Known devices for thermal therapy treatment have temperature control devices which are as described, for example, in European patents EP 2 194 940 B1 and EP 2 462 906 B1. These temperature control devices comprise a cooling unit and/or a heating unit by means of which a fluid, preferably water, is cooled and/or heated to the desired temperature. Preferably, one or more pumps are also provided, by means of which the temperature-controlled fluid is conveyed, via connecting hoses, to a heat transfer device.

DE 20 2018 107 423 U1 shows an example of a heat transfer device by means of which the heat generated by the temperature control device is transferred to the selected region of the body. The device shown there, which, in this document, as well as in practice is usually referred to as a cuff, comprises a first and a second flexible material layer between which flow spaces are provided through which the tempered fluid flows. These cuffs can be constructed in many different shapes for a predetermined region of the body, for example as a hand cuff, forearm cuff, knee cuff, calf cuff, round cuff, chest cuff or face cuff. Further, they can be constructed as trapezoidal cuffs or surface cuffs, which, depending on their size and shape, are suitable for being placed on any desired region of the body. Fasteners, tapes and the like are used to secure the cuffs to the body.

Although the devices mentioned above have proven themselves in practice, there is a desire for further improvement. It is therefore an object of the present invention to improve the device already known.

Features of aspects of the invention, as well as their preferred embodiments described below, can be combined with one another in any desired manner, as far as this is not expressly excluded or technically impossible. This relates to apparatus aspects and method aspects alike, as well as their preferred embodiments. Accordingly, for example, any of the devices disclosed herein can be used in the context of any of the methods disclosed herein. Further, for example, the heat transfer unit of the third aspect can be used with, or form part of, a device according to the first aspect or the fourth aspect. In order to avoid repetitions, features of certain embodiments will only be explained in connection with one of the aspects of the invention, it being understood that the same, corresponding or similar features can also form part of, or be used in connection with, embodiments of the other aspects of the invention.

The disclosure of the documents EP 2 194 940 B17-07-27, EP 2 462 906 B17-07-27, DE 20 2018 107 423 U1 mentioned above, as well as DE 10 2015 003 473 A1 are hereby incorporated by reference in the disclosure of the present invention.

The device in accordance with the first aspect of the invention has a temperature control device which is provided in order to control a temperature of a temperature control fluid. For this purpose, the temperature control device is connected, in a fluid conducting manner, to a heat transfer device, which is arranged to transfer heat to the selected region of the body, and is further arranged to temper the heat transfer device with a heat transferring temperature control fluid flowing through the heat transfer device. The device further comprises a control device which is connected to the temperature control device and to the heat transfer device, whereby the control device is arranged to control the temperature control device in order to cause the heat transfer device to be at least partially at an approximately uniform temperature in the region of a contact surface between the heat transfer device and the selected region of the body to be temperature controlled.

The term “control device” is intended to be understood to mean a device which either controls, and/or controls with feedback, parts of the device on the basis of data or values supplied to it and/or data or values or settings entered by a user. The influencing is preferably carried out via actuating devices. An actuating device is intended to be understood to mean any electrical or mechanical component which is suitable for influencing a technical system in a directed manner.

In this regard, the selected region of the body of a human may be any region on the surface of the body. In particular, the selected region may concern one of the limbs, such as an arm or a leg, preferably a hand or a foot. Further, the selected region may also concern a region of the chest, a region of the abdomen, a region of the back or a region of the head. In the following, the skin of the patient in the selected region is also referred to as a skin contact region.

A fluid connection, or a connection which is connected in a fluid conducting manner, is intended to be understood to mean a connection that allows the exchange of a liquid or a gaseous fluid from one location to another location. Typical fluid connections are preferably made via a hose or a pipe. The fluid connections are preferably partially or completely thermally insulated in order to keep the loss of heat or loss of cold as low as possible during the conduction of the fluid, in order to ensure, on the one hand, that an energy-saving construction can be achieved, and, on the other hand, to ensure that the target temperature which the heat transfer device is to reach in the region of the skin contact is maintained as accurately as possible.

According to the invention, a heat transferring temperature control fluid is used. The term “a heat transferring temperature control fluid” is intended to be understood to mean a fluid which, in terms of its function, is arranged to transport the heat stored in it, in the form of thermal energy, to a target location. Advantageously, a heat transferring temperature control fluid is therefore a liquid that is suitable for storing or absorbing a large amount of thermal energy. Preferably, water is used as the temperature control fluid, but it is also preferable to use a mixture of water and salt, or a suitable mineral oil or a synthetic oil.

In the context of the invention, the term “connected” can mean “directly connected”, such as preferably a cable or a hose, or “indirectly connected”, such as preferably via light, infrared, or radio according to the WiFi or Bluetooth standard. In this context, the temperature control device is directly connected to the heat transfer device, i. e. by means of at least one fluid line, while the temperature control device can also be indirectly connected to the control device, i. e. without a line, via radio or the like.

The region where a contact surface of the heat transfer device is located a short distance from the skin surface of the region of the body to be tempered and where it preferably rests directly on the skin surface is designated as the region of a contact surface between the heat transfer device and the region of the body to be tempered.

According to the invention, the heat transfer device is intended to generate an approximately uniform temperature on the selected region of the body to be tempered. In this regard, the term “an approximately uniform temperature” is intended to be understood to mean that all points in this region of the contact surface of the heat transfer device are within an interval of 10° C., preferably 5° C., particularly preferably 3° C., and further particularly preferably 1° C.

In a preferred embodiment, the heat transfer device comprises, for this purpose, at least one heat transfer unit, which is provided to be brought into contact with the selected region of the body. In this context, the heat transfer unit consists of a substantially flexible material in which one or more temperature control fluid chambers are arranged through which the temperature control fluid can flow.

As a rule, the region of the body to be tempered is not flat, but has concave and/or convex regions. In the context of the present invention, it has been found that these features of unevenness can lead to the formation of individual air pockets between the heat transfer unit and the skin surface of the body to be treated, which air pockets thermally insulate the affected local region of the skin portions of the selected region from the heat transfer unit. As a result of this, the tempering of the selected region becomes uneven and the desired effects of the tempering, in particular an increase or a decrease in blood flow, do not occur evenly.

In order to reduce this effect of limited localized thermal insulation, the heat transfer device comprises a substantially flexible material in order to keep the distance between the heat transfer unit and the region to be tempered over the entire three-dimensional surface as small as possible, whereby the flexibility preferably allows it to lie directly over the selected region to be tempered.

In this context, the temperature control fluid chambers are arranged within the heat transfer unit in such a way that, when the temperature control fluid flows through the temperature control fluid chambers, the heat of the temperature control fluid is transferred as uniformly as possible to the region of the body to be tempered.

In a preferred embodiment, in order to transfer the heat as uniformly as possible, the substantially flexible material of the heat transfer unit comprises at least a first flexible material layer having at least a first skin contact surface which faces at least partially towards a selected region of the body of a human or of an animal, and at least a first temperature control fluid contact surface which faces away from the first skin contact surface. In addition, the heat transfer unit comprises at least a second flexible material layer having at least a second temperature control fluid contact surface, which, between itself and the first temperature control fluid contact surface of the first flexible material layer, at least partially delimits the one or more temperature control fluid chambers through which the heat transferring temperature control fluid can flow.

In this context, the heat transfer unit further comprises at least a first connecting line for supplying a heat transferring temperature control fluid to the heat transfer unit, and at least a second connecting line for discharging a heat transferring temperature control fluid from the heat transfer unit. The first and second connecting lines are connected to the temperature control device in order to heat or to cool the temperature control fluid to the desired temperature in a circulating system.

In this context, by using flexible materials, the heat transfer unit has at least a shape, or can assume such a shape, in which it covers and/or at least partially encloses the selected region of the body of a human or of an animal.

In a preferred embodiment, in order to reduce the effect of the localized thermal insulation by air pockets as described above, the heat transfer device further comprises a pressure device in order to generate, or to increase, a contact pressure of the heat transfer unit on the selected region of the body, in order to thereby reduce, at least partially or even substantially completely, the occurrence of thermally insulating air pockets between the heat transfer unit and the region to be tempered. In this context, the pressure device comprises at least a pressure unit and a support device, wherein the pressure unit is prevented, by the support device, from performing a movement in a direction opposite to the skin contact surface of the selected region.

The pressure unit is constructed to subject the heat transfer unit at least partially to a pressure, which is then absorbed as the contact pressure of the heat transfer device by the portion of the body to be treated. For this purpose, the pressure unit comprises at least one pressure chamber with a predetermined or a variable internal pressure.

The use of a pressure chamber which is filled with a fluid has particular advantages. In a pressure chamber which is filled with a fluid, the pressure within the fluid is always the same. This means that the heat transfer unit is pressed onto the skin portions of the selected region with a uniform pressure. As a result of this, the flexible material of the heat transfer unit can adapt particularly well to convex and/or concave regions of the selected region, as a result of which the occurrence of air pockets is avoided, and a particularly good heat transfer is achieved.

In this context, the contact pressure represents that portion of the surface force which is transferred from the pressure unit via the heat transfer unit to the selected region of the body to be tempered.

A support device is provided in order to build up the contact pressure. The term “support device” is intended to be understood to mean any type of device that is suitable for absorbing surface forces that are oriented in a direction against the direction of the contact pressure.

In a preferred embodiment, the at least one pressure unit comprises a chamber which is filled with a pressure fluid, wherein the at least one chamber which is filled with a pressure fluid is bounded by a flexible material. The term “pressure fluid” is intended to be understood to mean a fluid that can be compressible, preferably air or a gas, or incompressible, preferably water, a mixture of water and salt, a mixture of water and oil, or an oil. However, it is also possible to use other fluids as pressure fluid.

In a preferred embodiment, the at least one chamber filled with a pressure fluid is connected to a pressure line. In this context, the pressure fluid in the at least one chamber filled with a pressure fluid can be subjected to pressure, either manually by means of muscle power by a user, and/or by means of a compressor, via the pressure line that is connected to the at least one chamber filled with a pressure fluid. As a result of this, an internal pressure in the at least one pressure chamber filled with a pressure fluid can be varied. As a result of the variable internal pressure, the contact pressure of the heat transfer device on the portion of the body is thus also adjustable. Preferably, a device is provided which is actuated by means of the muscular force of a human.

In this context, the term "compressor" is intended to be understood to mean a machine that serves the purpose of supplying mechanical work to the pressure fluid and thereby increasing the internal pressure. If the fluid is a liquid, the compressor represents a pump.

In one embodiment, the pressure device comprises a release valve for lowering the internal pressure of the pressure unit.

In a further preferred embodiment, the at least one pressure unit is not formed of a pressure chamber filled with a pressure fluid, but is made of an elastic material, and is also arranged between the support device and the heat transfer unit. Here, the elastic material may be a type of foam rubber, a type of rubber, or a combination of these or similar materials. In this context, the elasticity can be constant over the volume of the pressure unit, but, in some embodiments, it is also conceivable that the elasticity of the pressure unit varies over the volume in order to avoid possible pressure peaks, and/or to apply an increased pressure in a targeted manner, preferably over small radii of the portion of the body to be treated.

In an alternative embodiment, the pressure device comprises at least one pressure unit and a support device, wherein the pressure unit is attached to the support device, and the pressure unit is provided so as to at least partially subject the heat transfer unit to a pressure, wherein the pressure unit comprises a body of an elastic material which is adapted to at least partially increase a contact pressure of the heat transfer device on the selected region. Accordingly, the pressure unit does not need to comprise a pressure chamber. Instead, the body of elastic material itself has sufficient elasticity so that, when the body of elastic material is compressed, it can subject the heat transfer unit to a pressure. Again, the elastic material may be a type of foam rubber, a type of rubber, or a combination of these or similar materials.

The compression of the elastic material can be achieved, for example, by the elastic material being compressed between the support device and the portion of the body to be treated. For example, if the portion of the body to be treated is a hand, the heat transfer device may comprise a hand cuff or a glove or similar, in which the hand may be introduced. Assuming for example a generally symmetric construction, in one embodiment, the heat transfer device could be made up of three layers, whereby each layer effectively forms a pouch: an innermost pouch comprising the at least one heat transfer unit, which is located inside an intermediate pouch comprising the at least one pressure unit, which is located inside an outermost pouch comprising the support device (vaguely similar to the layers of an onion). In this example, the different portions of the heat transfer device (in particular the at least one heat transfer unit, the pressure unit and the support device), in particular their thicknesses, may be dimensioned such that, in the initial state of the heat transfer device (i.e. without the hand inserted), there is little or no space in the innermost pouch, i.e. little or no space in which to insert the hand. Preferably, there is also only little or no space between the innermost pouch and the intermediate pouch, and also between the intermediate pouch and the outermost pouch. When the hand is inserted in the innermost pouch, the material of the pressure unit (i.e. the intermediate pouch) is compressed between the support device (i.e. the outermost pouch) and the hand, with the heat transfer unit (i.e. the innermost pouch) being located between the pressure unit and the hand. The compression of the pressure unit in turn generates a pressure on the heat transfer unit, which may ensure good (thermal) contact between the heat transfer unit and the skin of the hand.

The same or a similar effect can be achieved with other configurations of heat transfer devices, for example heat transfer devices in the form of a forearm cuff, boot or the like. Likewise, a corresponding effect can be achieved if the portion of the body to be treated is not intended to be inserted into the heat transfer device, but if, instead, the heat transfer device is intended to be placed (unilaterally) against the skin of the human or animal to be treated. In this case, the heat transfer device may comprise several layers (e.g. three layers, such as an outer support device layer facing away from the skin, an intermediate layer constituting the pressure unit, and an inner heat transfer device layer facing towards the skin), rather than pouches which are placed one inside the other.

In one embodiment, the pressure unit has a volume, wherein (substantially) the entire volume of the pressure unit is made of the elastic material. This contrasts with pressure units which include a significant portion of substantially non-elastic material, which might negatively impact the elastic properties of the pressure unit. Further, this embodiment also contrasts with embodiments (described above) where the pressure unit forms a pressure chamber which can be filled with a pressure fluid.

More explicitly, in one embodiment, the pressure unit is non-inflatable. In this embodiment, the pressure or compression to be built up in the pressure unit could be generated by the pressure unit being compressed between the support device and the portion of the body to be treated, as described above.

Preferably, whether or not the pressure unit is inflatable, the material of the pressure unit is chosen from among a number of materials such that, in normal use (in particular when fixed to, held against, or wrapped around, a portion of the body to be treated, or when a portion of the body to be treated has been introduced into the heat transfer device) the pressure unit is compressed, at least in some areas, by at least 25%, at least 30%, at least 35%, at least 40%, at least 45%, at least 50%, at least 55%, or at least 60% of its thickness.

In a preferred embodiment, the support device of the pressure device is made of a material which has low flexibility.

In this context, the term "a material which has low flexibility" is intended to be understood to mean a material with a higher modulus of elasticity, such as preferably hard plastic. Above all, it is important here that the material which is used for the support device has a higher stiffness than the pressure unit, in order to conduct the internal pressure of the pressure unit to the contact surface between the heat transfer unit and the selected region of the body and the heat transfer unit.

In one embodiment, the support device may comprise, or be made of, plastics material, for example a sheet of plastics material. The plastics material may, for example, have a thickness selected from at least 0.5 mm, at least 0.8 mm, at least 1 mm, at least 1.3 mm, at least 1.5 mm and at least 1.7 mm. In addition, or as an alternative, the plastics material may, for example, have a thickness selected from at most 2.5 mm, at most 2.2 mm, at most 2 mm, at most 1.8 mm, at most 1.5 mm and at most 1.2 mm. The plastics material may, for example, have a thickness of about 1 mm, 1.3 mm or 2 mm.

In one embodiment, the support device is made of, or comprises, a material having a modulus of elasticity of at least $2\times10^9$ $Nm^{-2}$. By way of contrast, the pressure unit may be made of, or may comprise, a material having a modulus of elasticity of $0.5\times10^9$ $Nm^{-2}$ or less, preferably $0.2\times10^9$ $Nm^{-2}$ or less, preferably $0.1\times10^9$ $Nm^{-2}$ or less.

In one embodiment, the flexibility of a material of the pressure unit is significantly greater than the flexibility of the support device, in particular greater at least by a factor selected from the group consisting of 2, 3, 4, 5, 10, 20, 50 and 100. In one embodiment, this degree of flexibility can be expressed via the modulus of elasticity of the material in question.

In a preferred embodiment, the support device of the pressure device around the selected region of the body of a human or of an animal further comprises a connecting device with at least one fixing element. In this context, the connecting device is constructed in such a way that it at least partially reaches around the pressure device and, in this "reaching around" position, exerts supporting forces onto the pressure device, which at least partially contribute to fixing the pressure device in a "deployed for use" condition to the selected region of the body of a human or of an animal. In this context, the connecting device having at least one fixing element may be continuously adjustable, such as preferably by means of a strap, or may include dedicated attachment points, such as preferably press studs, or may consist of a combination of both.

The term "'deployed for use' condition" is intended to be understood to mean a condition in which the heat transfer device is applied to the selected region of the body.

In a preferred embodiment, at least one sensor device is further provided, which is connected to the control device. The sensor device is preferably arranged to measure a sensor signal at specific positions of the device. Preferably, the sensor device is used to measure the temperature and/or the contact pressure between the selected region of the body and the skin contact surface and/or in the heat transfer device and/or in an edge region of the heat transfer device which faces towards the body.

The term "sensor device" is intended to be understood to mean any device that has a sensor for measuring a physical state and which is set up to convert this state into a sensor signal. Here, the sensor signal can be optical, acoustic or digital.

In a preferred embodiment, the at least one sensor device is a plurality of sensor devices, which are preferably at least partially arranged in a grid, preferably in the edge region, or on the surface of the first material layer which, in the "deployed for use" position, faces towards the skin. In this context, the grid may be a grid with identical distances, or a grid with almost identical distances, or a grid with different distances, or a combination thereof.

Here, in a preferred embodiment, the measured sensor signal is selected from the group of pressure, electric current and temperature. However, other physical variables are also conceivable.

In a preferred embodiment, at least one display device is provided. The display device is connected to the control device and is set up to output the sensor signal measured by the sensor device to a user via the display device.

In this context, the display device can comprise any form of display facility that enables information to be provided to a user about the status of the individual devices and/or the measured sensor signal. Thus, the display can be visual, preferably in the form of a screen, acoustic, preferably in the form of an audible sound, but also haptic, preferably in the form of a vibration. However, other forms of display are also conceivable.

A temperature control device is provided in order to supply to, or remove from, the heat transferring fluid, the energy necessary for the temperature control of the selected region of the body. The temperature control device preferably has a housing, preferably a temperature control fluid supply device by means of which a heat transferring temperature control fluid is provided in the housing, and at least one temperature control unit, which is preferably arranged in the housing and by means of which the heat transferring temperature control fluid is temperature controlled. Further, the temperature control device has at least one temperature control fluid outflow device, through which the heat transferring temperature control fluid is led out of the housing at a substantially predetermined temperature, and preferably at least one pumping device, which is preferably arranged in the housing and which applies pressure to the heat transferring temperature control fluid flowing through the housing.

The temperature control unit preferably comprises an electric heating unit. Further preferably, the temperature control unit comprises at least one conventional cooling unit in which a refrigerant is compressed, expanded via a thermal expansion valve and condensed via a condenser.

Particularly preferably, the temperature control unit has, in addition or exclusively, at least one temperature control element which is constructed as a thermoelectric element, in particular as a Peltier element. Preferably, a heat exchange element through which a temperature control fluid can flow is also provided, in order to transfer heat to, or from, the temperature control fluid, and preferably at least one cooling unit.

Preferably, the device uses at least one of the three groups of sensors described in the following.

A first group of sensors is provided to detect the condition of the heat transfer device and, if applicable, the connecting lines as well.

This includes temperature sensors that sense the temperature at predetermined locations of the heat transfer device and the connecting lines, pressure sensors that measure the pressure forces of the pressure unit within the heat transfer device, and sensors for flow measurement by means of which the flow rate and/or the amount of temperature control fluid which is being supplied and/or discharged can be detected.

A second group of sensors is provided within the temperature control unit. Here, too, temperatures, pressure and flow velocity or flow volume are preferably detected.

A third group of sensors is provided for taking measurements of physiological data on the patient, which are preferably used by the control device to control, and/or control with feedback, the operation of the device and in particular the temperature of the heat transfer device.

Preferably, temperature sensors are used, which are preferably arranged in the form of thin electrodes in the selected region of the body to be tempered by the device. Furthermore, pressure sensors are preferably used, also preferably in the form of thin electrodes, by means of which the contact pressure of the heat transfer device can be detected.

Further preferably, sensors are used which detect the physiological state of the patient being treated. For this purpose, one or more sensors are selected from a subgroup which comprises the sensors mentioned in the following: sensors that measure the heart rate, sensors that record an ECG, sensors that measure the blood pressure, and preferably sensors that measure the blood flow.

In a preferred embodiment, the control device is set up to form one or more control loops on the basis of the signal(s) measured by the sensor devices or sensors, in such a way that a region of a contact surface between the heat transfer device and the portion of the body to be tempered has, at least in one region, an approximately uniform, preselected temperature.

The device preferably has one or more actuating or feedback control devices that allow parameters of the device such as the temperature of the fluid, the flow rate, the amount of fluid delivered, and the like to be changed. These actuating or feedback control devices may be electrical feedback control devices that preferably have an influence on a voltage, a frequency and/or a current. Further preferably, the feedback control devices may be mechanical feedback control devices that can preferably change the flow resistance and/or stop the flow, or they can be electromechanical in construction.

The control device is equipped with at least one, preferably however with two, or further preferably with a plurality of operating elements which enable the desired treatment parameters to be set. Preferably, this includes the specification of operating times and stand down times, as well as the specification of temperatures or temperature intervals.

Depending on the area of application, when the device is used for cooling, the following temperature ranges are particularly advantageous and should be covered by the respective device. For use in hospitals etc., a temperature range of 10-35° C. is recommended, for hospital and outpatient treatments a temperature range of 12-22° C., and for treatment in a private setting a temperature range of 15-22° C. However, it is also preferred to construct the device in such a way that it covers a wider temperature range of 10-35° C., or even a temperature range of 10-43° C.

Preferably, the control device comprises a processor device and a memory device. One or more program routines are preferably stored in the memory device, which, individually or together, are used to influence or to control, by means of the processor device, the operation of the control device and preferably also parts of the device. The program routines are preferably predetermined and permanently stored in the memory device. Further preferably, the program routines can be modified by the user and/or additional program routines can be entered into the memory device.

In particular, but not exclusively, in the case of a device that is used only, or also, in a private setting outside a hospital or other medical facility, part or all of the control of the control device may be performed by an external processor device. Preferably, a stationary or transportable computer, such as preferably a laptop computer, is used for this purpose. Further preferably, a mobile communication device, in particular a cell phone or particularly preferably a smartphone, is used as the external processor device. Preferably, the mobile communication device, in particular a smartphone, is connected to external sensors that can detect physiological data of the patient. Preferably, sensors that can be attached to the body of the patient are used for this purpose, such as for example wristbands with sensors, or a smartwatch. The programs used on the mobile communication device for collecting physiological data, such as preferably the heart rate and ECG functions, can then be used to control the device.

Preferably, the device features an alarm mode. This alarm mode is preferably triggered when a temperature is not within a desirable range. Preferably, this may be the case when the fluid temperature rises above a predetermined value or when, further preferably, a housing temperature assumes a value that is not desired. Further, the alarm mode may also be triggered when the physiological values which the sensors which are connected to the patient detect are within a range that is not desired.

In the examples, mentioned above, in accordance with the invention, there is provided a method of operating a device for carrying out thermal therapy treatment of a selected region of the body of a human or of an animal, wherein the method comprises the following steps. At the start, a heat transfer device is brought into a "deployed for use" condition in contact, by means of a pressure device, with the selected region of the body. A contact pressure acting on the selected region of the body is then applied via the pressure device. The selected region of the body is tempered via a temperature control device connected to the heat transfer device, in that a heat transferring temperature control fluid flows through a heat transfer unit of the heat transfer device, so that in the region of a contact surface between the heat transfer device and the portion of the body to be tempered has an approximately uniform temperature in at least one region.

The term "bringing the heat transfer device into contact" can preferably be understood to mean the placing of a cuff containing a heat transfer device around a hand of a patient. Further, the term "bringing into contact" can also be understood to mean the placing of a body part on a heat transfer device resting on a cushion.

In a preferred embodiment, the method further comprises the following step:

An internal pressure of a pressure unit of the pressure device is set, wherein the pressure unit comprises at least one chamber which is filled with a pressure fluid.

In this context, the internal pressure of the at least one chamber filled with a pressure fluid can be manually adjusted via muscle power of a user and/or via an external pressure source.

In a preferred embodiment, the method further comprises the following steps:

A sensor signal is measured via a sensor device connected to the heat transfer device.

A pressure device which is connected to a control device is then controlled via the control device on the basis of the measured sensor signal. This form of controlling can also be referred to as a control loop.

In the following, therapeutic treatments will be described for which the device in accordance with the invention is particularly suitable:

A targeted heat treatment before a surgical procedure improves the capillary circulation and promotes the healing after the procedure. To this end, heat is applied several times about 18 hours before the operation using the device in accordance with the invention, whereby tempering of the tissue to 41-43° C. is particularly advantageous. This tempering is applied, for example, three times for half an hour each time, interspersed by a cooling phase at room temperature, which also lasts half an hour each time.

For this purpose, a sequence program is stored or entered in the device, which sequence program controls the timing and the various components of the device. It is particularly preferred that physical data (temperature, pressure, etc.) or physiological data is used for this purpose, which is measured by means of the sensors.

After a surgical intervention, but also in particular after injuries and in the case of chronic diseases and any swelling resulting therefrom, internal bleeding, hematomas, edema and inflammation, cooling of the affected tissue with the device in accordance with the invention promotes the healing process and reduces the intensity of pain, which can result in a significantly reduced administration of drugs. This therapeutic effect can be explained by the fact that the affected tissue reacts to the intervention or the injury with inflammation and thus overheating, as a result of which the oxygen demand is increased. Cooling of the tissue reduces this oxygen demand and prevents cell death. To this end, the device is controlled in such a way that a specific target temperature is reached. For example, the target temperature for achieving the cooling of the tissue may be 14.5° C. Whether the target temperature has been reached can be monitored by the sensors, and additionally the physiological condition of the patient can be monitored, and the control device can be switched off, if necessary, if the values for the heart rate, blood flow or the like are in a range that is not desired.

Thermal therapeutic measures also have a particular significance in the treatment of cancer by means of chemotherapy. The chemotherapeutic agent which is used to reduce cancer cells penetrates into the blood capillaries of the hands and feet and can lead to the feared chemotherapy-induced polyneuropathy (CIPN) or hand-foot syndrome (HFS) with permanent damage to the tissue and in particular the nerve cells. In mild cases, this manifests itself as disagreeable skin sensations, "tingling" and the like; in severe cases it manifests itself as extensive or complete numbness, which can make it difficult to use the hands or even to walk. Furthermore, pain with sometimes high intensity is also reported. In severe cases, onycholysis, i. e. the detachment of one or more nails, also frequently occurs.

According to common understanding, the preferential attack of the sensitive nervous system is due to the blood supply of these nerve cells with fenestrated capillaries. This means that the protein composition of the cell wall is different, i. e. more permeable, to certain chemotherapeutic agents. Thus, they unfold elementary damage to the nerve cells. The damage to the cellular DNA, as well as the mitochondrial DNA, a disturbed calcium balance and oxidative stress promote the dissolution of the ganglion cells. Since the longest nerve fibers are more sensitive to these damaging influences, CIPN usually presents itself as length-dependent, with an emphasis on the lower extremities.

The cooling of the hands and feet or other regions of the body during chemotherapy with the device in accordance with the invention has the effect of reducing the oxygen demand of the cooled tissue and/or reducing the metabolism in the cooled regions and/or reducing blood flow to these regions, as a result of which less therapeutic agent reaches the blood capillaries and the development of polyneuropathy can be prevented. This can also advantageously be achieved with the device in accordance with the invention and with the method of operating the device in accordance with the invention.

The cooling of the hands and feet or other regions of the body during chemotherapy with the device in accordance with the invention also has the effect of reducing the excretion of chemotherapeutic agents from the sweat glands, thereby reducing the likelihood of HFS development.

The cooling is preferably carried out in a temperature range between 8° C. and 30° C., but particularly preferably in a range between 10° C. and 14° C. A cooling temperature in the range of 10° C. to 12° C. is even more preferred.

Preferably, the thermal treatment which has been explained above in relation to surgical procedures is also applied to the treatment in connection with chemotherapy in the form of a cold treatment. To this end, the device in accordance with the invention is preferably used to apply cold about 30 min prior to the administration of the chemotherapeutic agent, whereby tempering of the tissue surface or skin surface of the selected region to 10° C. to 12° C. is particularly advantageous. This tempering is preferably applied during the entire administration of the chemotherapeutic agent, as well as preferably for 1 hr to 3 hr after the completion of the administration of the chemotherapeutic agent.

Preferably, cytostatic drugs such as for example carboplatin, capecitabine, 5-Fu, cyclophosphamide, cytarabine, docetaxel, doxorubicin, oxaliplatin, paclitaxel, sorafinide and sunitinib are used as the chemotherapeutic agents for chemotherapy. These designations are trade names that are protected for the respective manufacturing or distribution companies. The list of these chemotherapeutic agents is not to be understood as a limitation. Embodiments of the present invention can be used in connection with other chemotherapeutic agents, in particular those which can result in CIPN, HFS and other side effects discussed herein, in particular those chemotherapeutic agents which can result in side effects which can be reduced or even eliminated through cooling of the hands and/or feet and/or other body parts of the patient undergoing the chemotherapeutic treatment.

In order for the optimum cooling temperature to be able to be set for each patient, the temperature control device can set the temperature control fluid with an accuracy of 1° C., but preferably with an accuracy of between 0.5° C. and 0.2° C. In order for the desired therapeutic effect to be achieved, it can be essential in the present context that the desired temperature, which is also referred to as the target temperature in the present description, is maintained as accurately as possible also during the cooling process.

In this application in connection with chemotherapy, the device is particularly advantageously equipped with a pressure device. Since the aim is to reduce the blood flow through the blood capillaries, it is of particular advantage here if the heat transfer unit is in uniform contact, i. e. as far as possible without any thermally insulating air pockets, with the skin regions of the selected region of the body of the patient. This is achieved by means of the pressure device.

For example, by means of time control of the device, the time which is required to reach the target temperature can be specified before the delivery of the chemotherapeutic agent is started.

However, temperature sensors on the heat transfer device can also be used instead to detect when the target temperature has been reached and then to output a corresponding signal.

Finally, a sensor for measuring blood flow can also be used here in a particularly advantageous manner. The cooling process is then started and continued until the blood flow has dropped to a predetermined value. By monitoring the patient's physiological values through the device, such as the heart rate and the blood pressure, it can be ensured at the same time that the cooling does not lead to an undesirable condition of the patient.

In one embodiment, the method is carried out at the same time as a chemotherapy treatment of the body of the human or animal, and is preferably started at least 20 minutes, preferably at least 30 minutes, before a start of the chemotherapy treatment, and/or is carried on until at least 20 minutes, preferably at least 30 minutes, preferably at least 40 minutes, preferably at least 1 hour, after an end of the chemotherapy treatment. This may provide good protection against certain side effects of chemotherapy treatment whilst not being overly time-consuming.

In one embodiment, the chemotherapy treatment is part of a sequence of chemotherapy treatments which are performed on the body of the human or animal, wherein the method is carried out at the same time as all chemotherapy treatments of said sequence of chemotherapy treatments. The inventor has found that the method in accordance with the invention produces best results (i.e. in terms of reducing or eliminating certain side effects of chemotherapy treatment) if it is carried out every time a chemotherapy treatment takes place. The start and finish time of the thermal treatment in relation to the start and finish time of the chemotherapy treatment (e.g. 30 minutes beforehand; 1 hour afterwards) may be kept the same for all chemotherapy treatments of the sequence of chemotherapy treatments, or may be varied.

In one embodiment, the method is carried out a number of times after a last chemotherapy treatment of said sequence of chemotherapy treatments, wherein said number is selected from the group consisting of 1, 2, 3 and 4. In this way, better protection from certain side effects of chemotherapy treatment can be provided than if no thermal treatment after the last chemotherapy treatment is carried out.

In one embodiment, the method is carried out a last time between 6 months and 18 months after the last chemotherapy treatment of said sequence of chemotherapy treatments. In this way, better protection from certain side effects of chemotherapy treatment can be provided than if the last thermal treatment is carried out at the same time as the last chemotherapy treatment, or only shortly afterwards (e.g. within one month).

In one embodiment, the chemotherapy treatment is part of a sequence of chemotherapy treatments which are performed on the body of the human or animal, wherein the method is carried out only once symptoms of chemotherapy-induced polyneuropathy (CIPN) or hand-foot syndrome (HFS) have been observed on the body of the human or animal. Since CIPN and HFS do not occur in every patient undergoing chemotherapy, it may in some cases be preferred to only carry out the thermal treatment if and when CIPN and HFS actually occur, although the results tend to be better (in terms of a long-term prevention of these symptoms) if the thermal treatment is performed as a prophylactic measure, as described above.

In one embodiment, the chemotherapy treatment is part of a sequence of chemotherapy treatments which are performed on the body of the human or animal, wherein the method is carried out only once symptoms have been observed on the body of the human or animal which relate to a grade according to Common Terminology Criteria for Adverse Events (CTCAE) v5.0, wherein said grade is selected from the group consisting of:

Grade 1 or higher,
Grade 2 or higher,
Grade 3 or higher, and
Grade 4.

The grades according to Common Terminology Criteria for Adverse Events (CTCAE) v5.0 are explained further below.

In the examples mentioned above, it is assumed that the temperature control device heats or cools the selected region to a specific target temperature. However, instead of a constant target temperature, the temperature can also be changed during the treatment. This can be done by modulating the temperature/time curve. This modulation can preferably have a rectangular shape, a sinusoidal shape, a sawtooth shape or a trapezoidal shape in the temperature/time curve.

Also disclosed herein is a heat transfer unit which is intended to be brought into contact with a selected region of the body of a human or of an animal and which is arranged to transfer heat to the selected region of the body, the heat transfer unit being for use with a temperature control fluid arranged to flow through the heat transfer unit, wherein the heat transfer unit comprises:

a first flexible material layer having a first skin contact surface which is arranged to face at least partially towards the selected region of the body, and having a first temperature control fluid contact surface which faces away from the first skin contact surface, a second flexible material layer having a second temperature control fluid contact surface, which, between itself and the first temperature control fluid contact surface of the first flexible material layer, at least partially delimits one or more temperature control fluid chambers through which a heat transferring temperature control fluid can flow, wherein the first flexible material layer and the second flexible material layer together are folded over or are arranged to be folded over, in particular by hand, generally along a folding line or folding region so as to define a first heat transfer unit portion comprising or defining a first temperature control fluid chamber portion and a second heat transfer unit portion comprising or defining a second temperature control fluid chamber portion, wherein the heat transferring temperature control fluid is arranged to flow from the first temperature control fluid chamber portion to the second temperature control fluid chamber portion passing the folding line or folding region, wherein, in the folding region or at or near the folding line, the heat transfer unit comprises a stiffening material to counteract a reduction in the flow of the heat transferring temperature control fluid from the first temperature control fluid chamber portion to the second temperature control fluid chamber portion via the folding line or folding region when the first flexible material layer and the second flexible material layer together are folded over generally along the folding line or folding region.

The first flexible material layer and the second flexible material layer can, for example, comprise flexible sheets of plastics material. During manufacture, these can for example be placed one on top of the other and connected to one another as described below. Before or during use, the combination of first and second flexible material layers is then folded over, to result in the heat transfer unit which, as a result of the layers having been folded over, has a sandwich structure of (at least) four layers: Each of the top and bottom layers of the 4-layer sandwich structure would be made up of, for example, (one half of) the second flexible material layer, and each of the middle two layers of the 4-layer sandwich structure would be made up of (one half of) the first flexible material layer. In this 4-layer sandwich structure, the bottom two layers would form part of the first heat transfer unit portion, and the top two layers would form part of the second heat transfer unit portion.

The heat transfer unit of the third aspect is in particular, but not exclusively, suitable for use in the treatment of a hand. When the heat transfer unit is used in the course of the treatment of a hand, the hand would be placed between the two middle layers of the 4-layer sandwich structure, whereby the two heat transfer unit portions on either side of the folding line or folding region can be (and remain during treatment) relatively flat panels, the folding region effectively acting as a hinge between the two relatively flat panels. More generally, the heat transfer unit of the third aspect is in particular, but not exclusively, suitable for use in the treatment of a body portion where two heat transfer unit portions, which may or may not be relatively flat, are connected at a folding line or folding region.

As it is envisaged that the temperature control fluid would enter the heat transfer unit via the first heat transfer unit portion and leave the device via the second heat transfer unit portion, the temperature control fluid needs to be able to flow from the first heat transfer unit portion (or the first temperature control fluid chamber portion) to the second heat transfer unit portion (or the second temperature control fluid chamber portion). The present inventor has found that, without the stiffening material, there is the risk that, once the first and second flexible material layers have been folded over, the cross-section of the temperature control fluid chamber is reduced near the folding line or folding region, which represents a resistance against the fluid flow, thereby reducing the flow rate of the temperature control fluid or even preventing the fluid flow altogether. In accordance with this aspect of the invention, the stiffening material helps to counteract this, so that the available cross-section of the temperature control fluid chamber near the folding line or folding region is held open, at least in part, or at least more than would be the case without the stiffening material. Accordingly, pursuant to this aspect of the invention, a higher flow rate can be achieved than in the case of a heat transfer unit without stiffening material. Alternatively, the same flow rate can be achieved with a less powerful pump when compared with a heat transfer unit without stiffening material.

When the first and second material layers are folded over, they will typically not fold along a predefined, well-defined folding line, in particular not necessarily along a straight line, given the flexible nature of the first and second material layers. Accordingly, the term “folding line” is preferably not intended to be understood in a mathematical sense, but instead in the sense of a region or volume in which the folding takes place. The term “folding region” can be understood in the same or a similar way. In particular, the term “folding region” is preferably understood to mean a region (volume) in which the flexible material of the first and second material layers is bent or distorted as a result of these layers being folded over. In particular, this may include a region in which at least one of these layers adopts the appearance of a wavy surface or similar, due to the material being “pushed together” as a result of these layers being folded over.

In one embodiment, the stiffening material is inserted between the first flexible material layer and the second flexible material layer. This represents a particularly simple yet effective way of providing the required stiffness in the folding region or at or near the folding line. It would however also be possible, either in addition or as an alternative, to integrate the stiffening material into the first and/or second flexible material layer.

In one embodiment, the stiffening material has a higher bending stiffness than a material of, or making up, the first flexible material layer and the second flexible material layer. In other words, the stiffening material resists bending more strongly that the material of the first and second flexible material layers. In preferred embodiments, the stiffening material is made from a material which is different from the material of the first and second flexible material layers. However, it is also conceivable that the stiffening material is made from the same material as the first and second flexible material layers, whereby the higher bending stiffness of the stiffening material would be achieved by making the stiffening material thicker than the first and second flexible material layers.

In one embodiment, the stiffening material exhibits sufficient flexibility to enable the first flexible material layer and the second flexible material layer together to be folded over, in particular by hand, generally along the folding line or folding region. This increases the user comfort and may also ensure that the stiffening material does not, for example, pierce one or both of the flexible material layers.

Guided by the present disclosure, those skilled in the art will be able to select suitable materials for the stiffening material (and for the first and second flexible material layers) to ensure that the stiffening material has sufficient flexibility whilst providing the required stiffness to counteract a reduction in the flow of the temperature control fluid. In particular, the choice of material may also depend on the intended application, including:

- which part of the body is to be treated
- whether the user (patient) is a child or an adult
- whether the user (patient) is a human or an animal
- whether the user (patient) is a small animal or a large animal
- the size (or power) of a pump used to pump the temperature control fluid through the device.

In one embodiment, the first flexible material layer and the second flexible material layer are connected, in particular via welding lines or fusion lines, in particular along the periphery of the first flexible material layer and the second flexible material layer, and/or along lines within the periphery of the first flexible material layer and the second flexible material layer, thereby in particular defining a labyrinth-type pattern along which, or through which, the heat transferring temperature control fluid can flow. This represents a simple yet effective way of forming the temperature control fluid chamber (portions). If the first and second flexible material layers are made of a plastics material, these can be welded or fused together through the application of heat. Preferably, the locations of the welding lines or fusion lines are selected such that the entire fluid entering the device is forced to flow through the temperature control fluid chamber (portions) in such a way that the fluid flow covers, or is guided past, substantially the entire surface of the first and second material layers, to ensure a substantially even temperature distribution.

In one embodiment, the stiffening material comprises one or more stiffening ribs, in particular extending from a location in the first heat transfer unit portion, in particular from a location within the first temperature control fluid chamber portion, to a location in the second heat transfer unit portion, in particular to a location within the second temperature control fluid chamber portion, passing the folding line or folding region. This simple yet effective solution can ensure that the stiffening material can perform its function of counteracting a reduction in the flow of the temperature control fluid in those areas where this is beneficial.

For example, a stiffening rib can be placed between the first and second flexible material layers before these are welded or fused together. Alternatively, the stiffening rib can be inserted between the first and second flexible material layers through a hole in one of the layers, for example at a location of a (future) welding line or fusion line, whereby the hole can be closed after insertion of the stiffening rib by welding or fusion.

In certain embodiments, the stiffening ribs have rounded ends, which may reduce the risk of a stiffening rib piercing the first or second flexible material layer.

In one embodiment, the heat transfer unit comprises a plurality of webs connecting the first flexible material layer and the second flexible material layer, the webs forming individual islands or columns leaving spaces through which the heat transferring temperature control fluid can flow. Conveniently, the webs can be formed from the first and/or second material layers by suitable molding processes. The webs can help to locate the first and second flexible material layers with respect to one another and may also help to keep the first and second flexible material layers at a distance from one another.

In one embodiment, the one or more stiffening ribs are inserted into respective ones of said spaces. The webs defining the spaces may therefore help to retain the stiffening ribs in place.

In one embodiment, the one or more stiffening ribs have a cross section which varies along a longitudinal direction of the stiffening ribs, in particular wherein the one or more stiffening ribs comprise one or more barbs or other projections. This may also help to retain the stiffening ribs in place, for example as a result of the barbs or other projections engaging the webs.

Also disclosed herein is a device for use in the thermal therapy treatment of at least two selected regions of the body of a human or of an animal, and in particular for use in the treatment of tissue damage after surgical interventions, of injuries, of inflammations and of chronic diseases of the rheumatic type, and in particular for assisting chemotherapeutic treatments, comprising:

a temperature control device which is provided in order to control a temperature of a temperature control fluid;

at least two heat transfer units which are respectively arranged to transfer heat to the at least two selected regions of the body, wherein the temperature control device is connected, in a fluid conducting manner, to the at least two heat transfer units, and is further arranged to temper the at least two heat transfer units with the temperature control fluid flowing through the at least two heat transfer units, wherein the at least two heat transfer units are connected in series so that the temperature control fluid is arranged to flow in the following order:

a) from the temperature control device to a first one of the at least two heat transfer units;

b) through the first one of the at least two heat transfer units;

c) from the first one of the at least two heat transfer units to a second one of the at least two heat transfer units;

d) through the second one of the at least two heat transfer units;

e) from the second one of the at least two heat transfer units back to the temperature control device.

Whilst devices with several heat transfer units for use in the thermal therapy treatment of regions of a body are known, these heat transfer units are individually connected to a respective temperature control device, whereby either a separate temperature control device is provided for each heat transfer unit, or two or more heat transfer units are connected to a single temperature control device, but each heat transfer unit is connected to a respective, dedicated pair of output and return ports of the temperature control device, i.e. only one heat transfer unit is supplied with temperature control fluid from each output port, making the entire device relatively complex. The present inventor has appreciated that two or more heat transfer units can be supplied with temperature control fluid from the same output port. In this context the inventor has further appreciated that the envisaged series connection of two or more heat transfer units is particularly effective if the heat transfer units of the series connection exhibit a relatively low fluid flow resistance—without this necessarily being intended to be understood as a limitation. This is in particular the case if there are no significant reductions in the cross-section of the temperature control fluid chamber(s) through which the temperature control fluid needs to flow. This can be achieved for example by avoiding sharp bends of the material of the heat transfer units and/or by using a stiffening material, for example in accordance with the third aspect of the invention.

In one embodiment, exactly two of the at least two heat transfer units are connected in series so that, after flowing through the second one of the exactly two heat transfer units, the temperature control fluid is arranged to flow back to the temperature control device without flowing through another one of the at least two heat transfer units. The inventor has found in experiments that, in many applications, connecting exactly two transfer units in series produces good results since the complexity of the device can be reduced (when compared with a device where only one heat transfer unit is supplied via a respective output port of the temperature control device) and yet the flow resistance of the series connection is kept relatively low so that a relatively low-power pump for circulating the temperature control fluid can be used.

In one embodiment, the first one of the at least two heat transfer units is arranged to provide temperature control for a foot and the second one of the at least two heat transfer units is arranged to provide temperature control for a hand. The inventor has found in experiments that, in many applications, this arrangement produces good results. For example, the shape of a typical foot is not as flat as the shape of a typical hand so that there is often no need for any sharp bends or folds in the (material of the) first heat transfer unit. The second heat transfer unit, being intended for the hand, may have a higher flow resistance, but as it is at a downstream location with respect to the first heat transfer unit, the somewhat higher flow resistance is less detrimental than if the heat transfer units were connected in reverse order. Again, the flow resistance can be (further) reduced by using the stiffening material in accordance with the third aspect of the invention, in one or both of the heat transfer units.

In one alternative embodiment, more than two of the at least two heat transfer units are connected in series so that, after flowing through the second one of the at least two heat transfer units, the temperature control fluid is arranged to flow through at least a further one of the at least two heat transfer units before flowing back to the temperature control device. This further reduces the complexity of device. In particular it may reduce the number of output and return ports necessary for circulating the temperature control fluid through the heat transfer units. Again, the flow resistance can be (further) reduced by using the stiffening material in accordance with the third aspect of the invention, in one or more of the heat transfer units, preferably in all of the heat transfer units.

In one embodiment, the first one of the at least two heat transfer units is arranged to provide temperature control for a foot, the second one of the at least two heat transfer units is arranged to provide temperature control for a foot, in particular a further foot, and any further ones of the at least two heat transfer units, if provided, are arranged to provide temperature control for a hand or hands. This embodiment again makes use of the fact that the flow resistance of a heat transfer unit for a foot tends to be lower than that of a heat transfer unit for a hand.

In one embodiment, the temperature control device has a separate output port and return port for each series connection of heat transfer units. This can ensure a substantially even temperature distribution in the respective heat transfer units. Alternatively, more than one series connection of heat transfer units could be connected to a single pair of output and return ports, whereby the series connections themselves would be connected in parallel to one another.

In one embodiment, at least one of the at least two heat transfer units, in particular the second one of the at least two heat transfer units, is a heat transfer unit in accordance with the third aspect of the invention.

Further advantageous embodiments of the invention are explained in the following description in connection with the accompanying drawings. In the drawings:

FIG. 10 shows a sectional view along line D-D of the heat transfer unit of FIG. 6;

FIG. 11 shows a sectional view along line D-D of the heat transfer unit of FIG. 6 in a folded state (and including the stiffening material);

FIG. 12 shows a sectional view of the heat transfer unit of FIG. 6 along a folding line;

FIG. 13 shows cross-sections of different embodiments of a stiffening rib;

FIG. 14 shows a side view of an embodiment of a stiffening rib;

Figure 1:
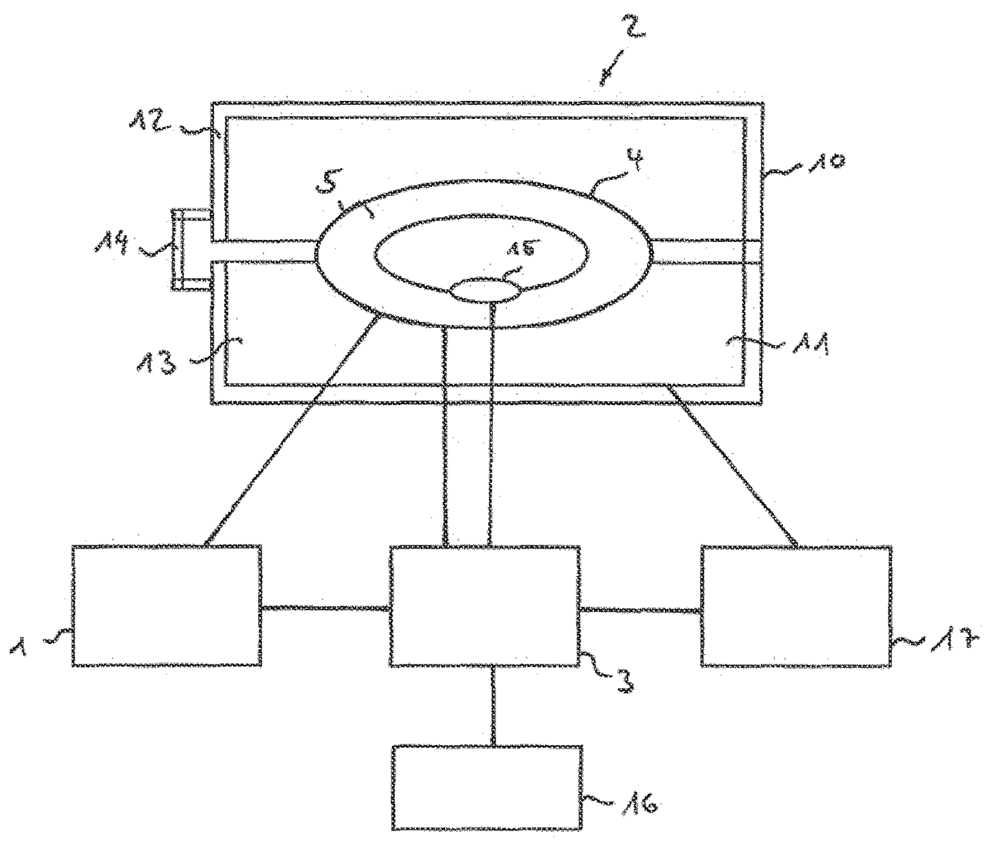
FIG. 1 shows a device in accordance with the invention for use in thermal therapy treatment.

FIG. 1 shows a device for use in the thermal therapy treatment of a selected region of the body of a human or of an animal, and in particular for use in the treatment of tissue damage after surgical interventions, of injuries, of inflammations and of chronic diseases of the rheumatic type, and in particular for the support of chemotherapeutic treatments, with a temperature control device 1, which is provided for tempering a temperature control fluid. The temperature control device 1 is connected, in a fluid conducting manner, to a heat transfer device 2, which is arranged for the transfer of heat to the selected region of the body, and which is further arranged to temper the heat transfer device 2 with a heat transferring temperature control fluid flowing through the heat transfer device 2. Furthermore, a control device 3 is connected to the temperature control device 1 and the heat transfer device 2, whereby the control device 3 is arranged to control the temperature control device 1 in order to cause the heat transfer device 2 to have at least partially an approximately uniform temperature in the region of a contact surface between the heat transfer device 2 and the selected region of the body to be tempered.

In this context, the heat transfer device 2 comprises at least one heat transfer unit 4, which is provided to be brought into contact with the selected region of the body, whereby the heat transfer unit 4 consists of a substantially flexible material, in which one or more temperature control fluid chambers 5 are arranged, through which the temperature control fluid can flow.

In this context, the heat transfer device further comprises a pressure device 10 which is adjacent to the heat transfer unit 4, wherein the pressure device 10 comprises at least one pressure unit 11 and a support device 12.

The pressure unit 11 is in communication with the support device 12, and the pressure unit 11 is provided in order to at least partially subject the heat transfer unit 4 to a pressure, which is then absorbed by the portion of the body to be treated as a contact pressure of the heat transfer device 2. For this purpose, the pressure unit 11 comprises at least one pressure chamber 13 with a predetermined or a variable internal pressure, and it is arranged to at least partially increase a contact pressure of the heat transfer device 2 on the selected region. In this context, the at least one pressure chamber 13 comprises a chamber which is filled with a pressure fluid, wherein the at least one chamber filled with a pressure fluid is formed by a flexible material. In this context, the pressure fluid in the at least one pressure chamber filled with a pressure fluid can be subjected to pressure via a pressure line which is connected to the at least one chamber filled with a pressure fluid, either manually via muscle power and/or with the help of a compressor 17, in order to change an internal pressure in the at least one chamber filled with a pressure fluid.

The support device 12 of the pressure device 10 further comprises a connecting device 14 which has at least one fixing element, and the connecting device 14 is constructed in such a way that it at least partially extends around the pressure device 10 and that it exerts supporting forces on the pressure device 10 in this surrounding position, which supporting forces at least partially contribute to fixing the pressure device 10 to the selected region of the body of a human or of an animal in a "deployed for use" condition.

Further, at least one sensor device 15 is provided, which is connected to the control device 3. The sensor device 15 is set up to measure a sensor signal between the selected region of the body and the skin contact surface. Here, the sensor signal can be present in optical, acoustic or digital form. In the example embodiment shown in FIG. 1, the sensor device 15 is mounted between the heat transfer unit 4 and the portion of the body to be treated, but other positions are also possible.

Further, at least one display device 16 is provided, wherein the display device 16 is connected to the control device 3 and is set up to output, to a user via the display device 16, the sensor signal which has been measured by the sensor device 15. The sensor signal can also be used for control with feedback, so that a region of a contact surface between the heat transfer device 2 and the portion of the body to be tempered has, at least in one region, an approximately uniform, preselected temperature.

Figure 2:
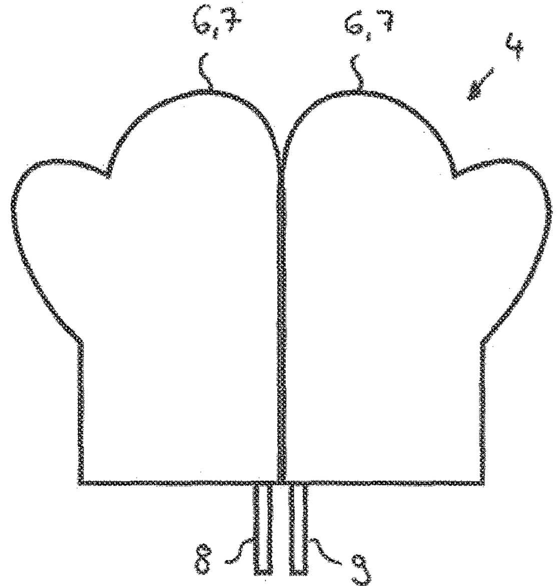
FIG. 2 shows a glove-shaped heat transfer unit in accordance with the invention in the unfolded state.

FIG. 2 shows a heat transfer unit 4 which is provided to be brought into contact with the selected region of the body, wherein the heat transfer unit 4 consists of a substantially flexible material in which one or more temperature control fluid chambers 5 (not shown) are arranged through which the temperature control fluid can flow.

In this context, the heat transfer unit 4 comprises:

at least a first flexible material layer 6 having at least a first skin contact surface which faces at least partially towards a selected region of the body of a human or of an animal, and having at least a first temperature control fluid contact surface which faces away from the first skin contact surface, at least a second flexible material layer 7 having at least a second temperature control fluid contact surface, which, between itself and the first temperature control fluid contact surface of the first flexible material layer 6, at least partially delimits one or more temperature control fluid chambers through which a heat transferring temperature control fluid can flow, wherein the heat transfer unit 4 further comprises:

at least a first connecting line 8 for supplying a heat transferring temperature control fluid to the heat transfer unit 4, at least a second connecting line 9 for discharging a heat transferring temperature control fluid from the heat transfer unit 4.

The use of flexible material layers 6, 7 is necessary because the region of the body to be tempered is not flat, but comprises concave and/or convex regions, and the flexibility of the material layers 6, 7 makes it possible to keep the distance between the heat transfer unit 4 and the region to be tempered as small as possible over the entire three-dimensional surface, whereby the heat transfer unit 4 preferably rests directly on the skin surface.

In this context, the heat transfer unit 4 has at least a first shape or can assume such a first shape in which it at least partially encloses the selected region of the body of a human or of an animal.

In a preferred variant, the heat transfer unit 4 has one of the following shapes, or can assume one of these shapes:

the shape of a cover enclosing the hand without subdivisions of the interior space;

the shape of a glove with partially separated covers for at least one finger, in particular the shape of a mitten with a partially separated cover for the thumb, as is shown in FIG. 2;

the shape of a finger glove with partially separated covers for each finger;

the shape of an at least partially fingerless glove, in which at least one finger is not enclosed.

However, the portion of the body to be treated can also be a foot or any other body part, in which case the heat transfer unit 2 has, or can assume, the shape of a shoe or stocking, or any other shape adapted to the respective body part.

Figure 3:
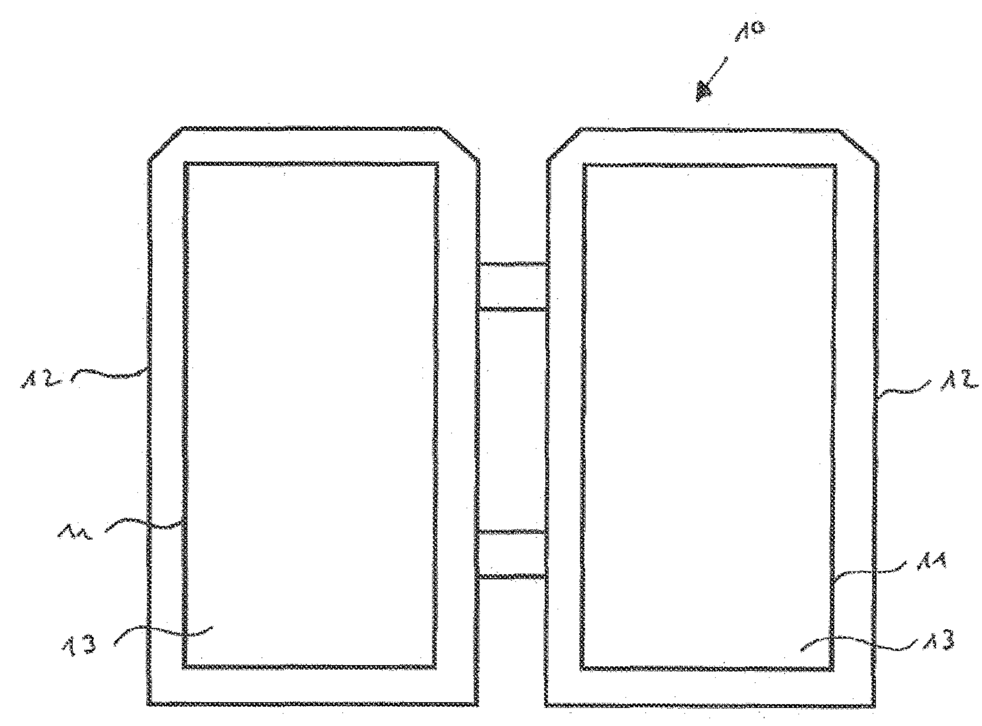
FIG. 3 shows a pressure device in accordance with the invention in the unfolded state.

FIG. 3 shows the pressure device 10, wherein the pressure device 10 comprises at least one pressure unit 11 and a support device 12, which is provided for building up a contact pressure. The pressure unit 11 is attached to the support device 12 and is provided for at least partially subjecting the heat transfer unit 4 to a pressure. For this purpose, the pressure unit 11 comprises at least one pressure chamber 13, which has a predetermined or a variable internal pressure and which is arranged to at least partially increase the contact pressure of the heat transfer device 2 on the selected region by means of the internal pressure. In this context, according to one embodiment, the pressure unit 11 may comprise a pressure chamber 13 in the form of a chamber which is filled with a pressure fluid, wherein the at least one chamber filled with a pressure fluid is delimited by a flexible material. In a further preferred embodiment, the at least one pressure unit 11 is made of an elastic material, such as preferably a type of foam rubber, a type of rubber, or a combination of these or similar materials, whereby the pressure unit 11 and the pressure chamber 13 are to be considered as the same component in this embodiment.

Figure 4:
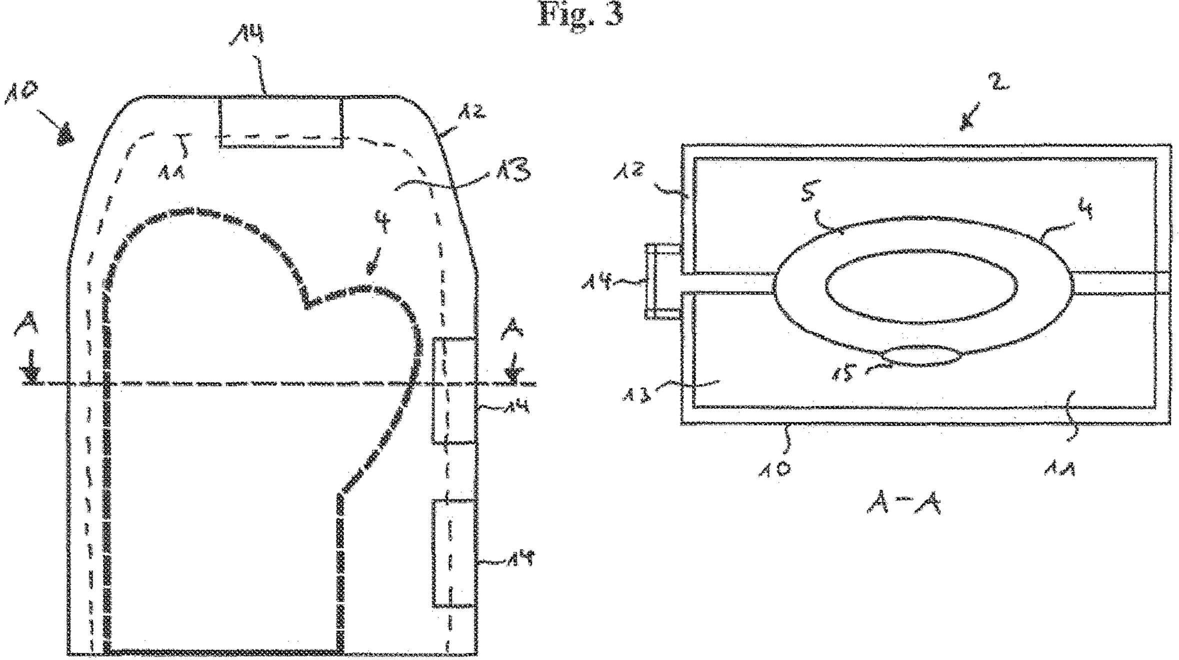
FIG. 4 shows a heat transfer unit in accordance with the invention in accordance with FIG. 1, in combination with a pressure device in accordance with the invention in accordance with FIG. 3.

FIG. 4 again shows the heat transfer device 2 from FIG. 1 and the pressure device 10 from FIG. 3 with slightly different dimensions. Here, the right-hand figure represents a section A-A through the section plane coming out of the plane of the drawing, along the dashed straight line A-A in the left-hand figure. In the left-hand figure, the heat transfer unit 4 of FIG. 2 is also indicated by dashed lines. Here, the heat transfer device 2 comprises at least one heat transfer unit 4, in which one or more temperature control fluid chambers 5 are arranged. A pressure device 10 is connected to the heat transfer unit 4, wherein the pressure device 10 comprises at least one pressure unit 11 and a support device 12. The support device 12 is attached to the pressure unit 11 and is provided so as to at least partially build up, via the heat transfer unit 4, a contact pressure of the heat transfer device 2 on the portion of the body to be treated. For this purpose, the pressure unit 11 comprises at least one pressure chamber 13. The pressure chamber 13 is arranged for at least partially increasing, by means of an internal pressure, the contact pressure of the heat transfer device 2 on the selected region. The pressure device 10 further comprises a support device 12, whereby the pressure device 10 is attached to the support device 12, and the pressure unit 11 is provided to at least partially subject the heat transfer unit 4 to a pressure. In this embodiment, the pressure device has three connecting devices 14, although preferably more, or fewer, connecting devices are conceivable. In this embodiment, each of the connecting devices 14 shown is of a one-piece construction; in a preferred embodiment, the connecting device is constructed in a circumferential manner, for example in the form of a zipper or a similar mechanism. In the embodiment shown in FIG. 4, the pressure unit 11 occupies a larger area, in a plan view, than the heat transfer unit 4, as well as being of one-piece construction, but, in relation to the heat transfer unit, smaller dimensions and multi-part pressure units are preferably also conceivable, which can be filled individually or jointly, through a common fluid connection, or can be controlled individually or jointly, with the help of a control device 3.

Figure 5:
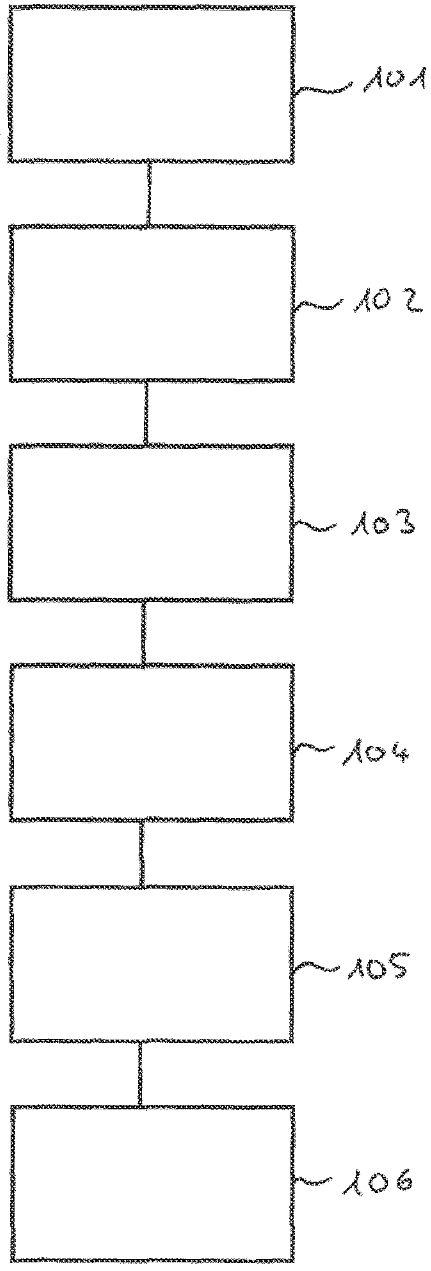
FIG. 5 shows a flow diagram of a method of operating the device in accordance with the invention.

FIG. 5 shows a flowchart of a method of operating a device for thermal therapy treatment of a selected region of the body of a human or of an animal in accordance with the invention, wherein the method comprises the following steps:

bringing a heat transfer device 2 with a pressure device 10 into contact 101 with the selected region of the body in a "deployed for use" condition;

applying 102, via the pressure device 10, a contact pressure acting on the selected region of the body, tempering 103, via a temperature control device 1 connected to the heat transfer device 2, the selected region of the body by causing a heat transferring heat control fluid to flow through a heat transfer unit 4 of the heat transfer device 2;

so that, in the region of a contact surface between the heat transfer device 2 and the portion of the body to be tempered, has an approximately uniform temperature in at least one region.

In a preferred embodiment, the method of operating a device for thermal therapy treatment further comprises the following step of:

adjusting 104 an internal pressure of a pressure unit 11 of the pressure device 10, wherein the pressure unit 11 comprises at least one chamber filled with a pressure fluid, wherein the internal pressure of the at least one chamber filled with a pressure fluid can be adjusted manually by means of muscle power of a user and/or by means of an external pressure source.

In a further preferred embodiment, the method of operating a device for thermal therapy treatment further comprises the following steps of:

measuring 105 a sensor signal by means of a sensor device 15 which is connected to the heat transfer device 2;

controlling 106, by means of a control device 3, the pressure device 10 which is connected to the control device 3, on the basis of the measured sensor signal.

In this context, the control device 3 is preferably set up in such a way that, together with the heat transfer device 2 and the temperature control device 1, it forms a control loop using the sensor signal measured by the sensor device 15, so that an approximately uniform, preselected temperature is feedback controlled in at least one region in the region of a contact surface between the heat transfer device and the portion of the body to be tempered. In this context, by avoiding thermally insulating air pockets between the heat transfer unit and the region of the body to be tempered, the heat transfer is significantly improved.

CLINICAL STUDY RESULTS/EXAMPLES

A number of studies have been carried out by, or on behalf of, the present applicant, details of which are given below. All of the studies were carried out in a confidential setting. The ambient temperature was at room temperature (about 22° C.).

Example 1

A device (a temperature control device, a heat transfer unit generally in the form of a hand cuff, as well as connecting hoses) in accordance with an embodiment of the present invention was used to cool a human hand. A temperature sensor was attached to the hand using several layers of adhesive tape. This way of attaching the temperature sensor to the hand was chosen so as to ensure, as far as reasonably possible, that the sensor measures the temperature of the skin of the hand rather than a temperature prevailing within a space between the skin and the hand cuff.

First, the skin temperature at different locations of the hand was measured without any cooling and without the hand being inserted in the hand cuff. The average temperature was about 29° C., with slight variations depending on the location on the hand (palm of the hand, back of the hand, or between fingers). All measurements were between 27° C. and 30° C.

Next, the hand was inserted in the hand cuff. Cooling fluid, in this case water, was cooled by the temperature control device and circulated between the temperature control device and the hand cuff. The target temperature of the cooling fluid was set to 10° C. on the temperature control device. The temperature control device kept the temperature of the cooling fluid stable at about 10° C.±0.5° C. (within the temperature control device). Due to thermal losses between the temperature control device and the hand cuff, the average temperature of the cooling fluid arriving at the hand cuff was about 11° C. Initially, no pressure (using a pressure device, as described above) was applied to generate an (additional) contact pressure between the hand cuff and the hand. After about 7 minutes, the hand temperature had gradually dropped to about 25° C. and remained approximately stable at that temperature.

Pressure was then applied by the pressure device so as to increase the contact pressure and to achieve a better (thermal) contact between the hand cuff and the hand. As a result, the temperature of the hand dropped more steeply than when the hand was first placed in the hand cuff without additional pressure. About 7 minutes after the beginning of the application of pressure, the hand temperature had gradually dropped to about 18° C. Eventually, the hand temperature settled at about 15° C. This was achieved approximately 18 minutes after the beginning of the application of pressure.

The pressure (as generated by the pressure device) was then removed but the hand cuff remained in place, and cooling fluid continued to be circulated. The hand temperature slowly increased again, by about 1° C. over the course of about 6 minutes. Once the hand cuff was removed completely, the temperature of the cooled hand increased only slowly, by about a further 3° to an average of about 19° (between 17° and 21°, depending on the location on the hand) over the course of a further 8 minutes.

Example 1 shows (inter alia) the following results:

a) The target temperature set on the temperature control device can differ significantly from the actual temperature measured at the skin temperature, in particular dependent on the contact pressure.

b) Even without the application of (additional) pressure, a reasonable degree of cooling can be achieved. A higher degree of cooling can be achieved through the application of (additional) pressure.

c) As the therapeutic effect is dependent on the temperature of the tissue to be cooled, certain embodiments of the present invention seek to ensure that the skin is actually cooled down to a target skin temperature. This produces better results than a therapy which merely ensures that the temperature of the cooling fluid (while still in the temperature control device) is cooled to a particular temperature whilst ignoring the actual skin temperature. The same applies if the therapy seeks to heat the tissue.

Example 2

The setup and the principle of the experiment in Example 2 corresponded in essence to that of Example 1, except that the experiment was carried out on a human foot instead of a human hand.

A device (a temperature control device, a heat transfer unit generally in the form of a slipper, as well as connecting hoses) in accordance with an embodiment of the present invention was used to cool a human foot. A temperature sensor was attached to the foot using several layers of adhesive tape. This way of attaching the temperature sensor to the foot was chosen so as to ensure, as far as reasonably possible, that the sensor measures the temperature of the skin of the foot rather than a temperature prevailing within a space between the skin and the slipper.

First, the skin temperature at different locations of the foot was measured without any cooling and without the foot being inserted in the slipper. The average temperature was about 31° C., with slight variations depending on the location on the foot (sole of the foot, back of the foot or between toes, here between the big toe and the second toe). All measurements were between 30° C. and 32° C.

Next, the foot was inserted in the slipper. Cooling fluid, in this case water, was cooled by the temperature control device and circulated between the temperature control device and the slipper. The target temperature of the cooling fluid was set to 10° C. on the temperature control device. The temperature control device kept the temperature of the cooling fluid stable at about 10° C.±0.5° C. (within the temperature control device). Due to thermal losses between the temperature control device and the slipper, the average temperature of the cooling fluid arriving at the slipper was about 11° C. Initially, no pressure (using a pressure device, as described above) was applied to generate an (additional) contact pressure between the slipper and the foot. After about 7 minutes, the foot temperature had gradually dropped to about 27° C. and remained approximately stable at that temperature.

Pressure was then applied by the pressure device so as to increase the contact pressure and to achieve a better (thermal) contact between the slipper and the foot. As a result, the temperature of the foot dropped. Depending on the location on the foot, this drop was slightly steeper than when the foot was first placed in the slipper without additional pressure. Between about 7 and 20 minutes (depending on the location on the foot) after the beginning of the application of pressure, the foot temperature had gradually dropped to about 22° C. Eventually, the foot temperature settled at about 17° C. (with some variation, depending on the location on the foot). This was achieved approximately 40 to 45 minutes after the beginning of the application of pressure.

The pressure (as generated by the pressure device) was then removed but the slipper remained in place, and cooling fluid continued to be circulated. The foot temperature slowly increased again, by about 1° C. over the course of about 6 minutes. Once the slipper was removed completely, the temperature of the cooled foot increased only slowly, by about a further 2° to an average of about 19° (between 17° and 20.5°, depending on the location on the foot) over the course of a further 8 minutes.

Example 2 shows similar results as Example 1, albeit with somewhat different rates of cooling and slightly different amounts of temperature variation depending on the location on the foot/hand.

Example 3

This clinical trial concerned 130 female patients with breast cancer, who underwent a taxane-based chemotherapy, in particular using Paclitaxel or Docetaxel. Before, during and after each chemotherapy treatment, their hands and feet were continuously cooled to about 10 to 12° C. (skin temperature) using a method/device according to an embodiment of the present invention. Cooling started 30 minutes before the chemotherapy treatment and continued for 30 to 60 minutes after the end of each chemotherapy treatment.

The occurrence of side-effects (adverse events, "AE") resulting from the chemotherapy was then recorded using the "Common Terminology Criteria for Adverse Events (CTCAE) v5.0". This uses clinical descriptions to define five grades depending on the severity of adverse events, plus a "Grade 0", as follows:

Grade 0 No AE observed.

Grade 1 Mild; asymptomatic or mild symptoms; clinical or diagnostic observations only; intervention not indicated.

Grade 2 Moderate; minimal, local or noninvasive intervention indicated; limiting age-appropriate instrumental ADL (Activities of Daily Living). Instrumental ADL refers to preparing meals, shopping for groceries or clothes, using the telephone, managing money, etc.

Grade 3 Severe or medically significant but not immediately life-threatening; hospitalization or prolongation of hospitalization indicated; disabling; limiting self care ADL. Self care ADL refers to bathing, dressing and undressing, feeding self, using the toilet, taking medications, and not bedridden.

Grade 4 Life-threatening consequences; urgent intervention indicated.

Grade 5 Death related to AE.

In this clinical trial, examples of Grade 2 AE were tingling, moderate numbness, reddening of the skin or other painful sensations. Examples of Grade 3 AE were extensive numbness, reduced ability of using arms and legs, the formation of blisters, skin flakes, bleeding of the skin, ulcerations or detachment of one or more fingernail or toenail, as well as strong pain.

In this clinical trial, the highest grade of AE reported during the entire course of the chemotherapy was:

Grade 0: 51 patients

Grade 1: 70 patients

Grade 2: 8 patients

Grade 3: 1 patient

Grade 4: 0 patients

Grade 5: 0 patients

In other words, using a method/device in accordance with an embodiment of the present invention, 93% of the patients (n=121) had no symptoms or only non-limiting symptoms (Grades 0 and 1), 6.2% (n=8) had Grade 2 symptoms and less than 1% (n=1) had Grade 3 symptoms. None of the patients had Grade 4 or 5 symptoms.

By way of contrast, in studies (involving a large number of patients) reported in scientific journals without the use of a method/device in accordance with an embodiment of the present invention, CIPN was reported in 60% of all patients, with one study reporting 4.1% and another study reporting 6-20% of patients with Grade 3 or 4 symptoms. Other studies reported that 50% of patients undergoing taxane-based chemotherapy (without the use of a method/device in accordance with an embodiment of the present invention) showed Grade 2 or 3 symptoms.

A comparison between, on the one hand, the clinical trial using a method/device in accordance with an embodiment of the present invention, and on the other hand, the studies reported in scientific journals, demonstrates that the methods/devices in accordance with the present invention significantly reduce the prevalence of AE from chemotherapy, and in particular the prevalence of AE in higher grades according to CTCAE v5.0.

Example 4

This clinical trial was based on the clinical trial of Example 3, i.e. the clinical trial of example 3 was followed by further treatments using a method/device in accordance with an embodiment of the present invention at four different points in time after the last chemotherapy treatment. These four points in time were chosen to be: 4 weeks, 4 months, 7 months and 10 months after the last chemotherapy treatment.

Whilst at the end of the chemotherapy treatment, 93% of the patients had no symptoms or only non-limiting symptoms (see example 3), this percentage increased to 98% at 10 months after the last chemotherapy treatment.

Example 5

This clinical trial was similar to the clinical trial of Example 3. This clinical trial concerned 38 female patients with breast cancer, who underwent a taxane-based chemotherapy, in particular using Paclitaxel or Docetaxel. However, initially they did not use a method/device in accordance with an embodiment of the present invention when they started their chemotherapy, and only did so once they developed symptoms of CIPN and/or HFS. They then carried on using the method/device in accordance with an embodiment of the present invention for all subsequent chemotherapy treatments and until 4 weeks after the last such treatment.

The prevalence of the symptoms according to CTCAE v5.0 was recorded at the time of the last chemotherapy treatment, and four weeks thereafter, i.e. the percentage of patients having symptoms of Grade 0, 1, 2 etc. In addition, the highest grade encountered during the period of observation was recorded. This produced the following results:

| | Grade 0 | Grade 1 | Grade 2 | Grade 3 |
|---|---|---|---|---|
| Highest Grade | 0% | 50% | 45% | 5% |
| Grade at last therapy | 16% | 59% | 22% | 3% |
| Grade at 4 weeks after last therapy | 31% | 50% | 17% | 2% |

The above results demonstrate a clear shift from symptoms in Grades 2 and 3 towards symptoms in Grade 0 (i.e. no symptoms) or in Grade 1 (non-limiting symptoms) during the time when a method/device in accordance with an embodiment of the present invention was used.

Example 6

The clinical trial of Example 5 was continued, i.e. a therapy in accordance with an embodiment of the present invention was provided at 4, 7, 10 and 14 months after the last chemotherapy treatment. The trend towards Grade 0 (no symptoms) or Grade 1 (non-limiting symptoms) continued during this additional period of observation.

Example 7

Further clinical trials similar to those of Examples 3 to 6 were carried out with patients undergoing chemotherapy to treat a variety of types of cancer, including breast, gynecological, and pancreatic cancer, and using a variety of chemotherapeutic agents such as those listed above. The results in terms of AE, in particular the shift towards lower grades (according to CTCAE v5.0) as a result of the treatment in accordance with an embodiment of the present invention), were generally similar to those of Examples 3 to 6.

Example 8

The setup and the principle of the experiment in Example 8 corresponded in essence to that of Examples 1 and 2. However, the temperature control device was set to a higher target temperature of between about 15° C. and 17° C. (instead of about 10° C.). It has been found that a skin temperature (hands and feet) of between about 20° C. and 22° C. is sufficient to significantly reduce the likelihood of negative (chemotherapy-related) effects developing (such as CIPN, for example). Using the higher target temperature of about 15° C. and 17° C. (as set on the temperature control device) was found to be sufficient to result in skin temperatures of between about 20° C. and 22° C. Subjects participating in this experiment reported that cooling the skin to about 20° C. and 22° C. (using a target temperature of about 15° C. and 17° C. as set on the temperature control device) feels more pleasant than cooling the skin to the somewhat lower temperature range used in Examples 1 and 2 (target skin temperature of about 15° C. and 17° C., using a target temperature of about 10° C. as set on the temperature control device).

Further Findings

Common to all of the above examples was that the vast majority of patients (about 75%) felt that the cold applied by the device in accordance with an embodiment of the present invention did not result in any particular discomfort. 89 patients were asked "how did you feel about the cold?"; their answers were:

Very comfortable: 33 patients
A bit cold: 33 patients
Cold: 14 patients
Very cold: 7 patients
Too cold: 2 patients This contrasts with previous treatments in which ice packs, ice buckets or similar were used to cool hands and/or feet, which is considered to be very uncomfortable by patients. In addition, and perhaps more importantly, such treatments often resulted in skin and tissue damage (frost burn/paralysis) and reactive hyperemia, whereas these side effects did not occur in the clinical trials in which a method/device in accordance with an embodiment of the present invention was used.

Further, the use of a method/device in accordance with an embodiment of the present invention did not appear to affect the efficacy of the chemotherapy treatment.

Heat Transfer Unit

Figures 6, 7, 8, 9:
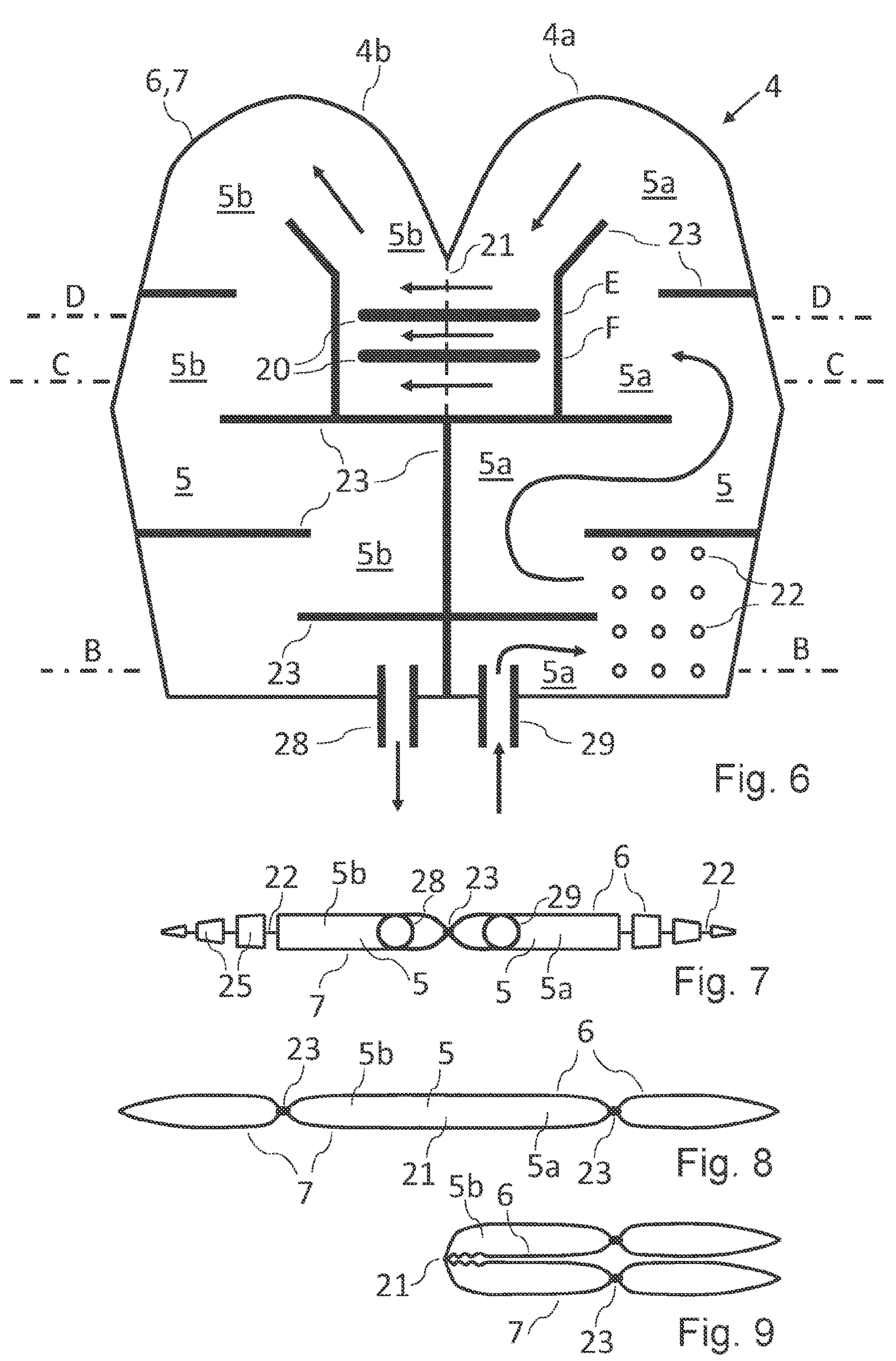
FIG. 6 shows a heat transfer unit in accordance with an embodiment of the invention for use in thermal therapy treatment.
FIG. 7 shows a sectional view along line B-B of the heat transfer unit of FIG. 6.
FIG. 8 shows a sectional view along line C-C of the heat transfer unit of FIG. 6.
FIG. 9 shows a sectional view along line C-C of the heat transfer unit of FIG. 6 in a folded state and if the stiffening material were omitted.

FIG. 6 shows a heat transfer unit 4 in accordance with an embodiment of the invention for use in thermal therapy treatment. As already mentioned, the heat transfer unit 4 can be used in connection with, or be part of, the device(s) of FIGS. 1 to 4. FIG. 7 shows a sectional view along line B-B of the heat transfer unit of FIG. 6, and FIG. 8 shows a sectional view along line C-C of the heat transfer unit of FIG. 6.

Referring to FIGS. 6 to 8 in combination, the heat transfer unit 4 comprises a first flexible material layer 6 and a second flexible material layer 7, which are placed one on top of the other. In an unfolded state as shown in FIGS. 6 to 8, the layers of flexible material 6, 7 are initially substantially flat. A control fluid chamber 5 is formed between the flexible material layers 6, 7. In order to form and delimit the control fluid chamber 5, the layers of flexible material 6, 7 can be connected to one another substantially along their entire periphery, either directly—for example by welding or fusing processes, in particular in case the flexible material layers are made of plastics material—or indirectly via an additional material (not shown). The heat transfer unit 4 or the control fluid chamber 5 is therefore sealed in a substantially fluid-tight manner, except that an input port 29 and an output port 28 are provided to enable a temperature control fluid to be supplied into, and to be discharged from, the control fluid chamber 5.

In the embodiment shown in FIG. 6, the heat transfer unit is formed with a number of welding lines or fusion lines 23. This can be formed by welding, fusing or otherwise connecting the layers of flexible material 6 and 7 in selected regions or along selected lines in such a manner that fluid is (substantially) prevented from flowing across these lines 23. Accordingly, lines 23 define a path which a temperature control fluid needs to take in order to pass from the input port 29 through the control fluid chamber 5 to the output port 28, as partly indicated by arrows (not labelled). Lines 23 can be regarded as defining a labyrinth pattern, whereby the pattern of lines as shown in FIG. 6 is merely one example; other patterns are also possible.

Lines 23 may also help to locate the first flexible material layer 6 with respect to the second flexible material layer 7 so that, in use, these layers remain substantially parallel to one another.

Layers 6 and 7 are also connected to one another by means of webs 22. These can again be formed by welding or fusing or otherwise connecting layers 6 and 7 to one another, for example by suitable molding processes. In the plan view of FIG. 6, webs 22 may appear as individual islands around which the temperature control fluid may flow. As shown in the cross-sectional view of FIG. 7, the webs 22 may take the form of individual columns, whereby their size and shape as shown in FIGS. 6 and 7 represents only one of many possibilities. Further, in the interest of a clear illustration, only some webs 22 are shown in the figures. It is to be understood that more, or fewer webs 22 can be provided, or even none at all. In particular, webs 22 may be distributed substantially over the entire surface of layers 6 and 7, and they may form a regular or irregular pattern. Webs 22 may also help to locate the first flexible material layer 6 with respect to the second flexible material layer 7 so that, in use, these layers remain substantially parallel to one another. Further, webs 22 may help to keep layers 6 and 7 spaced from one another at positions between adjacent webs. As shown in particular in FIG. 7, spaces 25 are formed between adjacent webs 22 so that the temperature control fluid can flow through these spaces 25.

The heat transfer unit 4 of the example shown in FIGS. 6 to 8 is made up of two halves or heat transfer unit portions 4*a* and 4*b*. Heat transfer unit portions 4*a* and 4*b* are mirror images of one another, although this is not essential. Accordingly, in a variant, heat transfer unit portion 4*b* could differ from a mirror image of heat transfer unit portion 4*a*. Each of the heat transfer unit portions 4*a*, 4*b* comprises (portions of) the two flexible layers 6, 7 described above.

In the example shown in FIGS. 6 to 8, heat transfer unit 4 is intended to be used to temper a human hand and each heat transfer unit portion 4*a*, 4*b* is therefore somewhat larger than a human hand. In use, one of the heat transfer unit portions (e.g. 4*b*) is folded over onto the other heat transfer unit portion (4*a*), as shown in FIGS. 9 and 11, generally along a folding line 21 which, in the example shown, is also the axis of symmetry of the two heat transfer unit portions 4*a*, 4*b* (or rather, the folding line 21 lies in a plane of symmetry perpendicular to the drawing plane). The hand to be tempered can be placed between the two heat transfer unit portions 4*a*, 4*b*, either before or after they are folded over. As shown in FIGS. 9 and 11, the folded heat transfer unit 4 forms a 4-layer structure, whereby the second flexible material layer 7 forms the top and bottom layers of the 4-layer structure and the first flexible material layer 6 forms the middle two layers of the 4-layer structure. The hand to be tempered would be placed between the middle two layers 6.

As shown in the lower half of FIG. 6, along much of the central folding line, the second temperature control fluid chamber portion 5*b* is separated from the first temperature control fluid chamber portion 5*a* by a welding line or fusion line 23. Accordingly, the temperature control fluid can only flow from the first temperature control fluid chamber portion 5*a* to the second temperature control fluid chamber portion 5*b* via that portion 21 of the folding line which is indicated in the top half of FIG. 6 by a dashed line 21. Here, the first and second flexible material layers 6, 7 are not connected to one another, at least not over the entire length of what is indicated by the dashed line 21.

FIG. 9 shows a sectional view along line C-C of the heat transfer unit of FIG. 6 in a folded state. However, this is shown without any stiffening material (to be explained below in more detail) and illustrates what would happen if the stiffening material were omitted. At or near the folding line 21, given the non-zero thickness of the heat transfer unit 4 (best seen in FIG. 8), the second layer of flexible material 7 has "a longer path" (as seen in FIG. 9) than the first layer of flexible material 6, with the result that a portion of the material of the first layer of flexible material 6 is pushed together and may form a region with a surface having a somewhat wavy appearance (left portion in FIG. 9). This portion can also be regarded as a folding region. Owing to the fact that the material of the first layer of flexible material 6 is pushed together in the folding region, the remaining cross-section of the control fluid chamber 5 near the folding line 21 or in the folding region (i.e. at the transition from the first temperature control fluid chamber portion 5*a* to the second temperature control fluid chamber portion 5*b*) is (significantly) reduced, which in turn may reduce the fluid flow. In some cases, the cross-section of the control fluid chamber 5 in the folding region may become zero. This may prevent the fluid flow altogether.

Pursuant to an embodiment of the invention, as shown in FIGS. 6, 10 and 11, a stiffening material 20 is used to counteract the reduction in fluid flow at the folding line 21 or in the folding region. As shown in FIG. 10, a stiffening rib 20 is placed, in particular inserted, between the first and second layers of flexible material 6, 7. The stiffening rib 20 may have a generally cylindrical form and/or may have rounded ends to reduce the risk of the stiffening rib 20 piercing one or both of the layers 6, 7.

The stiffening rib 20 has some flexibility to allow the heat transfer unit to be folded over along the folding line 21. On the other hand, the stiffening rib 20 has a higher bending stiffness than the layers of flexible material 6, 7.

The stiffening rib 20 may be placed in spaces 25 between webs 22. This is illustrated in FIG. 12, which shows a sectional view of the heat transfer unit 4 of FIG. 6 along the folding line 21. That is, for example the left-hand edge of FIG. 12 corresponds to a position at the lower end of the dashed line 21 in FIG. 6, and the right-hand edge of FIG. 12 corresponds to a position at the upper end of the dashed line 21 in FIG. 6. The viewing direction of FIG. 12 is from the right-hand side in FIG. 6 to the left-hand side.

As illustrated in FIG. 12, two stiffening ribs 20 are inserted into respective spaces 25. Adjacent spaces 25 remain empty. The number of stiffening ribs 20 and spaces 25 to be left empty is not limited to the particular embodiment shown and may depend, inter alia, on the materials used.

When the heat transfer unit 4 is folded over (FIG. 11), the stiffening material 20 is bent as well. The stiffening material 20 itself may obstruct much of the space 25 in which it is located. However, the presence of the stiffening material 20 in some of the spaces 25 also has the effect of preventing the collapse (of the type indicated in FIG. 9) of adjacent spaces 25 (which are left empty) so that temperature control fluid can continue to flow through these empty spaces 25 even when the heat transfer unit 4 is folded over.

FIG. 13 shows four examples of possible cross-sections of stiffening ribs 20, i.e. the shape of a ring, cross, star or square. The edges of the cross and the star shape may be rounded, as has been indicated for the square shape. In any event, these shapes are indicative only and are not to be understood in a limiting sense.

A stiffening rib 20 with a cross-section in the shape of a ring (i.e. a hollow cylinder) may permit temperature control fluid to flow through the stiffening rib 20 itself, which may increase the total fluid flow.

FIG. 14 shows a side view of an embodiment of a stiffening rib 20. The stiffening rib 20 of this particular embodiment may generally have a cylindrical form. However, it is additionally formed with barbs 24, e.g. flexible barbs 24, which project sideways with respect to the longitudinal extent of the stiffening rib 20. The angle between the barbs 24 and the longitudinal direction may for example be in the range of 20° to 60°. Alternatively, other projections could be formed on the outer surface of stiffening rib 20, for example semispherical projections. A mixture of barbs 24 and other projections is also possible. The barbs 24 or other projections may help to locate the stiffening ribs 20 within spaces 25, in particular by the barbs 24 or other projections engaging webs 22.

Stiffening ribs 20 can be placed between the flexible material layers 6, 7 before these are connected to one another, in particular by welding or fusing. Alternatively, the flexible material layers 6, 7 can be connected to one another first, and then the stiffening ribs 20 are inserted between the flexible material layers. To this end, a hole (not shown) can be formed in one of the flexible material layers 6, 7, for example at or near one of the welding lines or fusion lines 23, for example at the locations indicated by letters "E" and "F" in FIG. 6. The stiffening ribs 20 are then inserted through these holes to assume the location shown in FIG. 6, after which the holes can be closed, for example by welding or fusion processes.

In alternative embodiments (not explicitly shown in the drawings), stiffening material 20 can be integrated into one or both of the first and second layers of flexible material 6, 7, either instead of, or in addition to, the provision of one or more stiffening ribs 20 or similar between these layers.

Further, one or both of the first and second layers of flexible material 6, 7 may (each) be formed from two or more components layers. The expressions "first layer of flexible material" and "second layer of flexible material" are preferably understood to encompass structures made up of two or more such component layers.

Connecting Heat Transfer Units in Series

Figure 15:
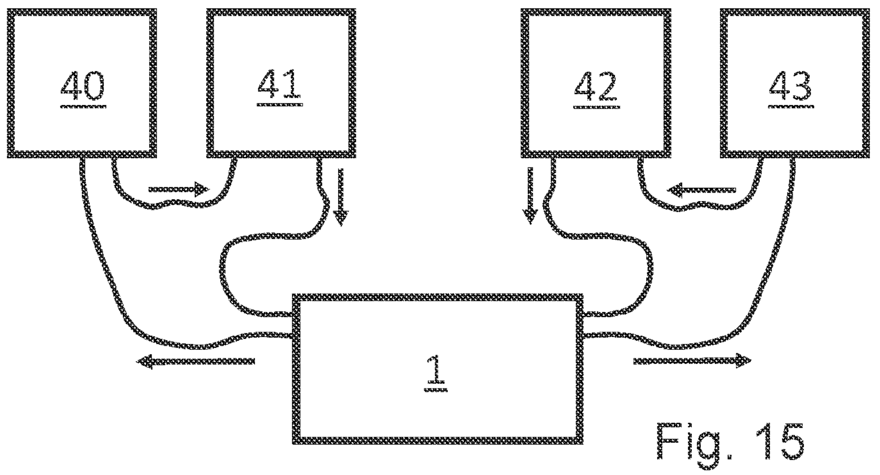
FIG. 15 shows a schematic diagram of a device for use in thermal therapy treatment according to an embodiment of the invention.

FIG. 15 shows a schematic diagram of a device for use in thermal therapy treatment according to an embodiment of the invention. As shown in FIG. 15, the device comprises a temperature control device 1 and four heat transfer units 40, 41, 42 and 43. One or more, in particular all, of these heat transfer units 40 to 43 may include stiffening material as described above in connection with FIGS. 6 to 13. Two series connections of heat transfer units are shown in FIG. 15: a first series connection comprising heat transfer units 40 and 41 and a second series connection comprising heat transfer units 43 and 42. Each of these series connections is connected to a respective pair of output and return ports (not labelled) of the temperature control device 1.

As indicated by arrows in FIG. 15, a temperature control fluid is supplied from an output port of temperature control device 1 to a first heat transfer unit 40. The fluid flows through the first heat transfer unit 40 and from there to a second heat transfer unit 41. After flowing through the second heat transfer unit 41, the fluid returns to the temperature control device 1 via a return port of the temperature control device 1. Accordingly, only one pair of output and return ports is used or is necessary to supply the temperature control fluid to two of the heat transfer units, i.e. 40 and 41. This embodiment also uses fewer supply lines between the temperature control device 1 and the heat transfer units 40, 41 when compared with implementations in which each heat transfer unit is connected to a dedicated pair of output and return ports of a temperature control device.

Without limitation, the first heat transfer unit 40 can for example be used to provide thermal therapy treatment for a foot, and the second heat transfer unit 41 can be used to provide thermal therapy treatment for a hand.

The second series connection can be operated in a corresponding manner, whereby the heat transfer unit 43 can be regarded as a first heat transfer unit of the second series connection and the heat transfer unit 42 can be regarded as a second heat transfer unit of the second series connection. The explanation provided above in connection with the first series connection can therefore also apply to the second series connection, mutatis mutandis.

Figure 16:
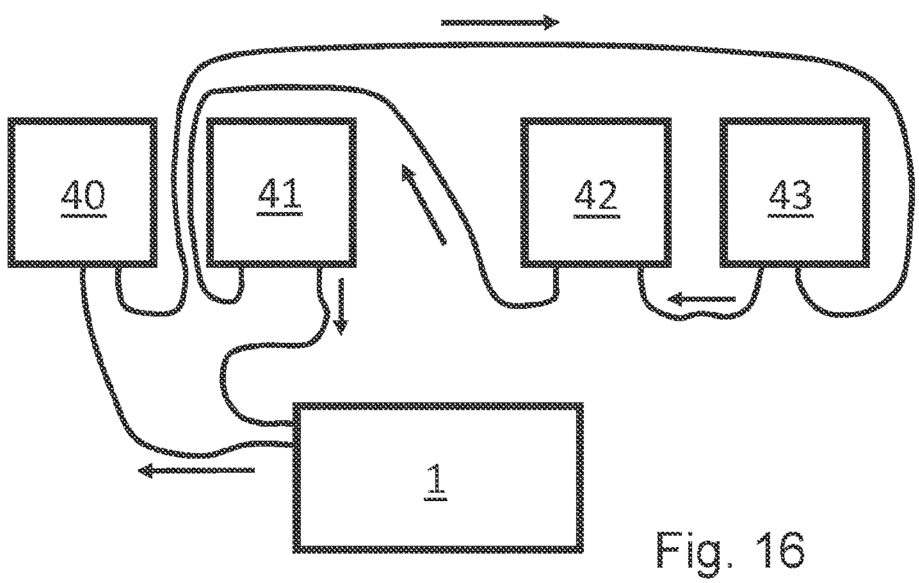
FIG. 16 shows a schematic diagram of a device for use in thermal therapy treatment according to a further embodiment of the invention.

FIG. 16 shows a schematic diagram of a device for use in thermal therapy treatment according to a further embodiment of the invention. The structure and principle of operation of this embodiment is similar to that of the embodiment shown in FIG. 15, except that all four heat transfer units 40 to 43 are connected in series. Accordingly, the temperature control fluid, after leaving the temperature control device 1 via its output port, first flows through heat transfer unit 40 (e.g. for a foot), then through heat transfer unit 43 (e.g. for a foot), then through heat transfer unit 42 (e.g. for a hand), then through heat transfer unit 41 (e.g. for a hand), and then back to the temperature control device 1 via its return port. In this embodiment, all four heat transfer units 40 to 43 can be supplied with temperature control fluid via a single pair of output and return ports of the temperature control device 1.

It is also possible to supply more, or fewer, heat transfer units from a single temperature control device 1 and/or via a single pair of output and return ports and/or in a series connection.

LIST OF REFERENCE SIGNS

1 temperature control device
2 heat transfer device
3 control device
4 heat transfer unit
4*a* first heat transfer unit portion
4*b* second heat transfer unit portion
5 temperature control fluid chamber 5*a* first temperature control fluid chamber portion
5*b* second temperature control fluid chamber portion
6 first flexible material layer
7 second flexible material layer
8 first connecting line
9 second connecting line
10 pressure device
11 pressure unit
12 support device
13 pressure chamber
14 connecting device
15 sensor device
16 display device
17 compressor
20 stiffening material/stiffening rib
21 folding line
22 web
23 welding line/fusion line
24 barb/projection
25 space
28 output port
29 input port
40 heat transfer unit (e.g. for a foot)
41 heat transfer unit (e.g. for a hand)
42 heat transfer unit (e.g. for a hand)
43 heat transfer unit (e.g. for a foot)
101 bringing into contact
102 applying
103 tempering
104 adjusting
105 measuring
106 controlling

The invention claimed is:

1. A heat transfer unit which is provided to be brought into contact with a selected region of a body of a human or of an animal and which is arranged to transfer heat to the selected region of the body, the heat transfer unit being for use with a temperature control liquid arranged to flow through the heat transfer unit, wherein the heat transfer unit comprises:

a first flexible material layer having a first skin contact surface which is arranged to face at least partially towards the selected region of the body, and having a first temperature control fluid contact surface which faces away from the first skin contact surface, a second flexible material layer having a second temperature control fluid contact surface, which, between itself and the first temperature control fluid contact surface of the first flexible material layer, at least partially delimits one or more temperature control fluid chambers through which a heat transferring temperature control liquid can flow, wherein the first flexible material layer and the second flexible material layer together are folded over or are arranged to be folded over, in particular by hand, generally along a folding line or folding region so as to define a first heat transfer unit portion comprising or defining a first temperature control fluid chamber portion and a second heat transfer unit portion comprising or defining a second temperature control fluid chamber portion, wherein the heat transferring temperature control liquid is arranged to flow from the first temperature control fluid chamber portion to the second temperature control fluid chamber portion passing the folding line or folding region, wherein, in the folding region or at or near the folding line, the heat transfer unit comprises a stiffening material to counteract a reduction in the flow of the heat transferring temperature control liquid from the first temperature control fluid chamber portion to the second temperature control fluid chamber portion via the folding line or folding region when the first flexible material layer and the second flexible material layer together are folded over generally along the folding line or folding region, and wherein the stiffening material is inserted into at least one of the one or more temperature control fluid chambers through which the heat transferring temperature control liquid can flow, between the first flexible material layer and the second flexible material layer.

2. The heat transfer unit according to claim 1, wherein the stiffening material has a higher bending stiffness than a material of, or making up, the first flexible material layer and the second flexible material layer.

3. The heat transfer unit according to claim 1, the stiffening material exhibits sufficient flexibility to enable the first flexible material layer and the second flexible material layer together to be folded over, in particular by hand, generally along the folding line or folding region.

4. The heat transfer unit according to claim 1, wherein the first flexible material layer and the second flexible material layer are connected, in particular via welding lines or fusion lines, in particular along a periphery of the first flexible material layer and the second flexible material layer, and/or along lines within the periphery of the first flexible material layer and the second flexible material layer, thereby in particular defining a labyrinth-type pattern along which, or through which, the heat transferring temperature control liquid can flow.

5. The heat transfer unit according to claim 1, wherein the stiffening material comprises one or more stiffening ribs, in particular extending from a location in the first heat transfer unit portion, in particular from a location within the first temperature control fluid chamber portion, to a location in the second heat transfer unit portion, in particular to a location within the second temperature control fluid chamber portion, passing the folding line or folding region.

6. The heat transfer unit according to claim 5, wherein the one or more stiffening ribs have a cross section which varies along a longitudinal direction of the stiffening ribs, in particular wherein the one or more stiffening ribs comprise one or more barbs or other projections.

7. The heat transfer unit according to claim 1, wherein a plurality of webs connecting the first flexible material layer and the second flexible material layer, the webs forming individual islands or columns leaving spaces through which the heat transferring temperature control liquid can flow.

8. The heat transfer unit according to claim 7, wherein the one or more stiffening ribs are inserted into respective ones of said spaces.

9. A device for use in a thermal therapy treatment of at least two selected regions of the body of a human or of an animal, and in particular for use in the treatment of tissue damage after surgical interventions, of injuries, of inflammations and of chronic diseases of a rheumatic type, and in particular for assisting chemotherapeutic treatments, comprising:

a temperature control device which is provided in order to control a temperature of a temperature control liquid;

at least two heat transfer units which are respectively arranged to transfer heat to the at least two selected regions of the body, wherein at least one of the heat transfer units comprises:

a first flexible material layer having a first skin contact surface which is arranged to face at least partially towards the selected region of the body, and having a first temperature control fluid contact surface which faces away from the first skin contact surface, a second flexible material layer having a second temperature control fluid contact surface, which, between itself and the first temperature control fluid contact surface of the first flexible material layer, at least partially delimits one or more temperature control fluid chambers through which a heat transferring temperature control liquid can flow, wherein the first flexible material layer and the second flexible material layer together are folded over or are arranged to be folded over, in particular by hand, generally along a folding line or folding region so as to define a first heat transfer unit portion comprising or defining a first temperature control fluid chamber portion and a second heat transfer unit portion comprising or defining a second temperature control fluid chamber portion, wherein the heat transferring temperature control liquid is arranged to flow from the first temperature control fluid chamber portion to the second temperature control fluid chamber portion passing the folding line or folding region, wherein, in the folding region or at or near the folding line, the heat transfer unit comprises a stiffening material to counteract a reduction in the flow of the heat transferring temperature control fluid from the first temperature control fluid chamber portion to the second temperature control fluid chamber portion via the folding line or folding region when the first flexible material layer and the second flexible material layer together are folded over generally along the folding line or folding region, and wherein the stiffening material is inserted into at least one of the one or more temperature control fluid chambers through which a heat transferring temperature control liquid can flow, between the first flexible material layer and the second flexible material layer, wherein the temperature control device is connected, in a fluid conducting manner, to the at least two heat transfer units, and is further arranged to temper the at least two heat transfer units with the temperature control liquid fluid flowing through the at least two heat transfer units, wherein the at least two heat transfer units are connected in series so that the temperature control liquid fluid is arranged to flow in the following order:

a) from the temperature control device to a first one of the at least two heat transfer units;

b) through the first one of the at least two heat transfer units;

c) from the first one of the at least two heat transfer units to a second one of the at least two heat transfer units;

d) through the second one of the at least two heat transfer units;

e) from the second one of the at least two heat transfer units back to the temperature control device.

10. The device according to claim 9, wherein exactly two of the at least two heat transfer units are connected in series so that, after flowing through the second one of the exactly two heat transfer units, the temperature control liquid is arranged to flow back to the temperature control device without flowing through another one of the at least two heat transfer units.

11. The device according to claim 9, wherein the first one of the at least two heat transfer units is arranged to provide temperature control for a foot and the second one of the at least two heat transfer units is arranged to provide temperature control for a hand.

12. The device according to claim 9, wherein more than two of the at least two heat transfer units are connected in series so that, after flowing through the second one of the at least two heat transfer units, the temperature control fluid is arranged to flow through at least a further one of the at least two heat transfer units before flowing back to the temperature control device.

13. The device according to claim 9, wherein the first one of the at least two heat transfer units is arranged to provide temperature control for a foot, the second one of the at least two heat transfer units is arranged to provide temperature control for a foot, in particular a further foot, and any further ones of the at least two heat transfer units, if provided, are arranged to provide temperature control for a hand or hands.

14. The device according to claim 9, the temperature control device has a separate output port and return port for each series connection of heat transfer units.

15. A method of performing thermal therapy treatment of at least two selected regions of the body of a human or of an animal, the method comprising:

providing a device according to claim 10;

causing the temperature control liquid to flow in the following order:

a) from the temperature control device to a first one of the at least two heat transfer units;

b) through the first one of the at least two heat transfer units;

c) from the first one of the at least two heat transfer units to a second one of the at least two heat transfer units;

d) through the second one of the at least two heat transfer units; and e) from the second one of the at least two heat transfer units back to the temperature control device.

* * * * *